US011918305B2

United States Patent
Bowling et al.

(10) Patent No.: US 11,918,305 B2
(45) Date of Patent: Mar. 5, 2024

(54) SYSTEMS AND METHODS FOR ESTABLISHING VIRTUAL CONSTRAINT BOUNDARIES

(71) Applicant: Stryker Corporation, Kalamazoo, MI (US)

(72) Inventors: David Gene Bowling, Los Ranchos De Albuquerque, NM (US); Donald W. Malackowski, Schoolcraft, MI (US); José Luis Moctezuma de la Barrera, Freiburg (DE); Patrick Roessler, Merzhausen (DE); Jerry A. Culp, Kalamazoo, MI (US); John Michael Stuart, Rio Rancho, NM (US); Joel N. Beer, Albuquerque, NM (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/891,288

(22) Filed: Aug. 19, 2022

(65) Prior Publication Data
US 2022/0387117 A1 Dec. 8, 2022

Related U.S. Application Data

(60) Continuation of application No. 16/685,442, filed on Nov. 15, 2019, now Pat. No. 11,464,579, which is a (Continued)

(51) Int. Cl.
*A61B 34/20* (2016.01)
*A61B 17/02* (2006.01)
(Continued)

(52) U.S. Cl.
CPC .............. *A61B 34/20* (2016.02); *A61B 17/02* (2013.01); *A61B 17/16* (2013.01); *A61B 34/30* (2016.02);
(Continued)

(58) Field of Classification Search
CPC ......... A61B 34/32; A61B 17/02; A61B 17/16; A61B 34/30; A61B 90/03; A61B 34/20;
(Continued)

(56) References Cited

U.S. PATENT DOCUMENTS 5,603,318 A  2/1997 Heilbrun et al.
5,820,623 A  10/1998 Ng
(Continued)

FOREIGN PATENT DOCUMENTS

CN  101254103 A  9/2008
EP     1545368 B1  3/2009
(Continued)

OTHER PUBLICATIONS

Khadem, R. et al., "Comparative Tracking Error Analysis of Five Different Optical Tracking Systems", Computer Aided Surgery, 2000, pp. 98-107, vol. 5, Stanford, CA, USA; 10 pages.
(Continued)

*Primary Examiner* — Stephen Holwerda
(74) *Attorney, Agent, or Firm* — Howard & Howard Attorneys PLLC

(57) ABSTRACT

A surgical system, method, and non-transitory computer readable medium involving a robotic manipulator configured to move a surgical instrument relative to virtual boundaries. A navigation system tracks each of a first object, a second object, and the surgical instrument. The first object is moveable relative to the second object. One or more controllers associate a first virtual boundary with the first object and associate a second virtual boundary with the second object. The first virtual boundary is moveable in relation to the second virtual boundary. The controller(s) control the robotic manipulator in relation to the first virtual boundary to facilitate interaction of the surgical instrument with the first object. The controller(s) control the robotic (Continued)

manipulator in relation to the second virtual boundary to avoid interaction of the surgical instrument with the second object.

14 Claims, 7 Drawing Sheets

Related U.S. Application Data continuation of application No. 15/416,717, filed on Jan. 26, 2017, now Pat. No. 10,512,509, which is a division of application No. 14/205,702, filed on Mar. 12, 2014, now Pat. No. 9,603,665.

(60) Provisional application No. 61/780,148, filed on Mar. 13, 2013.

(51) Int. Cl.
| | | |
|---|---|---|
| *A61B 17/16* | (2006.01) | |
| *A61B 34/30* | (2016.01) | |
| *A61B 34/32* | (2016.01) | |
| *A61B 90/00* | (2016.01) | |
| *A61B 17/00* | (2006.01) | |

(52) U.S. Cl.
CPC ............... *A61B 34/32* (2016.02); *A61B 90/03* (2016.02); *A61B 2017/00734* (2013.01); *A61B 2034/2048* (2016.02); *A61B 2034/2055* (2016.02); *A61B 2034/2061* (2016.02); *A61B 2034/2068* (2016.02); *A61B 2090/3937* (2016.02); *A61B 2090/3945* (2016.02); *A61B 2090/3983* (2016.02); *Y10S 901/09* (2013.01); *Y10S 901/47* (2013.01)

(58) Field of Classification Search
CPC .... A61B 2034/2061; A61B 2090/3945; A61B 2034/2048; A61B 2090/3937; A61B 2090/3983; A61B 2017/00734; A61B 2034/2068; A61B 2034/2055; Y10S 901/09; Y10S 901/47
See application file for complete search history.

(56) References Cited

U.S. PATENT DOCUMENTS

| | | | |
|---|---|---|---|
| 5,824,085 | A | 10/1998 | Sahay et al. |
| 5,871,018 | A | 2/1999 | Delp et al. |
| 5,880,976 | A | 3/1999 | DiGioia III et al. |
| 5,882,206 | A | 3/1999 | Gillio |
| 5,891,157 | A | 4/1999 | Day et al. |
| 5,950,629 | A | 9/1999 | Taylor et al. |
| 5,952,796 | A | 9/1999 | Colgate et al. |
| 5,971,976 | A | 10/1999 | Wang et al. |
| 5,976,156 | A | 11/1999 | Taylor et al. |
| 5,995,738 | A | 11/1999 | DiGioia, III et al. |
| 6,002,859 | A | 12/1999 | DiGioia, III et al. |
| 6,033,415 | A | 3/2000 | Mittelstadt et al. |
| 6,037,927 | A | 3/2000 | Rosenberg |
| 6,063,095 | A | 5/2000 | Wang et al. |
| 6,097,168 | A | 8/2000 | Katoh et al. |
| 6,102,850 | A | 8/2000 | Wang et al. |
| 6,157,873 | A | 12/2000 | DeCamp et al. |
| 6,205,411 | B1 | 3/2001 | DiGioia, III et al. |
| 6,228,089 | B1 | 5/2001 | Wahrburg |
| 6,233,504 | B1 | 5/2001 | Das et al. |
| 6,236,875 | B1 | 5/2001 | Bucholz et al. |
| 6,236,906 | B1 | 5/2001 | Muller |
| 6,304,050 | B1 | 10/2001 | Skaar et al. |
| 6,311,100 | B1 | 10/2001 | Sarma et al. |
| 6,314,312 | B1 * | 11/2001 | Wessels ................ A61B 34/20 606/130 |
| 6,322,567 | B1 | 11/2001 | Mittelstadt et al. |
| 6,329,778 | B1 | 12/2001 | Culp et al. |
| 6,330,837 | B1 | 12/2001 | Charles et al. |
| 6,336,931 | B1 | 1/2002 | Hsu et al. |
| 6,341,231 | B1 | 1/2002 | Ferre et al. |
| 6,347,240 | B1 | 2/2002 | Foley et al. |
| 6,351,659 | B1 | 2/2002 | Vilsmeier |
| 6,351,661 | B1 | 2/2002 | Cosman |
| 6,368,330 | B1 | 4/2002 | Hynes et al. |
| 6,377,839 | B1 | 4/2002 | Kalfas et al. |
| 6,385,475 | B1 | 5/2002 | Cinquin et al. |
| 6,385,509 | B2 | 5/2002 | Das et al. |
| 6,405,072 | B1 | 6/2002 | Cosman |
| 6,408,253 | B2 | 6/2002 | Rosenberg et al. |
| 6,413,264 | B1 | 7/2002 | Jensen et al. |
| 6,414,711 | B2 | 7/2002 | Arimatsu et al. |
| 6,421,048 | B1 | 7/2002 | Shih et al. |
| 6,423,077 | B2 | 7/2002 | Carol et al. |
| 6,430,434 | B1 | 8/2002 | Mittelstadt |
| 6,432,112 | B2 | 8/2002 | Brock et al. |
| 6,434,415 | B1 | 8/2002 | Foley et al. |
| 6,436,107 | B1 | 8/2002 | Wang et al. |
| 6,450,978 | B1 | 9/2002 | Brosseau et al. |
| 6,456,868 | B2 | 9/2002 | Saito et al. |
| 6,461,372 | B1 | 10/2002 | Jensen et al. |
| 6,466,815 | B1 | 10/2002 | Saito et al. |
| 6,473,635 | B1 | 10/2002 | Rasche |
| 6,490,467 | B1 | 12/2002 | Bucholz et al. |
| 6,491,702 | B2 | 12/2002 | Heilbrun et al. |
| 6,494,882 | B1 | 12/2002 | Lebouitz et al. |
| 6,501,997 | B1 | 12/2002 | Kakino |
| 6,514,082 | B2 | 2/2003 | Kaufman et al. |
| 6,514,259 | B2 | 2/2003 | Picard et al. |
| 6,520,228 | B1 | 2/2003 | Kennedy et al. |
| 6,522,906 | B1 | 2/2003 | Salisbury, Jr. et al. |
| 6,533,737 | B1 | 3/2003 | Brosseau et al. |
| 6,535,756 | B1 | 3/2003 | Simon et al. |
| 6,542,770 | B2 | 4/2003 | Zylka et al. |
| 6,552,722 | B1 * | 4/2003 | Shih ................ G06F 3/03545 345/419 |
| 6,620,174 | B2 | 9/2003 | Jensen et al. |
| 6,665,554 | B1 | 12/2003 | Charles et al. |
| 6,676,669 | B2 | 1/2004 | Charles et al. |
| 6,699,177 | B1 | 3/2004 | Wang et al. |
| 6,704,694 | B1 | 3/2004 | Basdogan et al. |
| 6,711,432 | B1 | 3/2004 | Krause et al. |
| 6,723,106 | B1 | 4/2004 | Charles et al. |
| 6,728,599 | B2 | 4/2004 | Wang et al. |
| 6,757,582 | B2 | 6/2004 | Brisson et al. |
| 6,778,867 | B1 | 8/2004 | Ziegler et al. |
| 6,785,572 | B2 | 8/2004 | Yanof et al. |
| 6,785,593 | B2 | 8/2004 | Wang et al. |
| 6,788,999 | B2 | 9/2004 | Green |
| 6,793,653 | B2 | 9/2004 | Sanchez et al. |
| 6,804,547 | B2 | 10/2004 | Pelzer et al. |
| 6,827,723 | B2 | 12/2004 | Carson |
| 6,837,892 | B2 | 1/2005 | Shoham |
| 6,871,117 | B2 | 3/2005 | Wang et al. |
| 6,892,112 | B2 | 5/2005 | Wang et al. |
| 6,929,606 | B2 | 8/2005 | Ritland |
| 6,951,538 | B2 | 10/2005 | Ritland |
| 6,963,792 | B1 | 11/2005 | Green |
| 6,978,166 | B2 | 12/2005 | Foley et al. |
| 6,999,852 | B2 | 2/2006 | Green |
| 7,006,895 | B2 | 2/2006 | Green |
| 7,035,716 | B2 | 4/2006 | Harris et al. |
| 7,055,789 | B2 | 6/2006 | Libbey et al. |
| 7,056,123 | B2 | 6/2006 | Gregorio et al. |
| 7,097,640 | B2 | 8/2006 | Wang et al. |
| 7,139,601 | B2 | 11/2006 | Bucholz et al. |
| 7,155,316 | B2 | 12/2006 | Sutherland et al. |
| 7,158,736 | B2 | 1/2007 | Sato et al. |
| 7,181,315 | B2 | 2/2007 | Watanabe et al. |
| 7,204,844 | B2 | 4/2007 | Jensen et al. |
| 7,206,626 | B2 | 4/2007 | Quaid, III |
| 7,206,627 | B2 | 4/2007 | Abovitz et al. |
| 7,215,326 | B2 | 5/2007 | Rosenberg |
| 7,239,940 | B2 | 7/2007 | Wang et al. |
| 7,249,951 | B2 | 7/2007 | Bevirt et al. |

(56) References Cited

U.S. PATENT DOCUMENTS

| | | | |
|---|---|---|---|
| 7,346,417 B2 | 3/2008 | Luth et al. | |
| 7,404,716 B2 | 7/2008 | Gregorio et al. | |
| 7,454,268 B2 | 11/2008 | Jinno | |
| 7,466,303 B2 | 12/2008 | Yi et al. | |
| 7,468,594 B2 | 12/2008 | Svensson et al. | |
| 7,543,588 B2 | 6/2009 | Wang et al. | |
| 7,561,733 B2 | 7/2009 | Vilsmeier et al. | |
| 7,573,461 B2 | 8/2009 | Rosenberg | |
| 7,625,383 B2 | 12/2009 | Charles et al. | |
| 7,648,513 B2 | 1/2010 | Green et al. | |
| 7,660,623 B2 | 2/2010 | Hunter et al. | |
| 7,683,565 B2 | 3/2010 | Quaid et al. | |
| 7,725,162 B2 | 5/2010 | Malackowski et al. | |
| 7,744,608 B2 | 6/2010 | Lee et al. | |
| 7,747,311 B2 | 6/2010 | Quaid, III | |
| 7,772,541 B2 | 8/2010 | Froggatt et al. | |
| 7,801,342 B2 | 9/2010 | Boese et al. | |
| 7,813,838 B2 | 10/2010 | Sommer | |
| 7,818,044 B2 | 10/2010 | Dukesherer et al. | |
| 7,824,424 B2 | 11/2010 | Jensen et al. | |
| 7,831,292 B2 | 11/2010 | Quaid et al. | |
| 7,835,784 B2 | 11/2010 | Mire et al. | |
| 7,892,243 B2 | 2/2011 | Stuart | |
| 7,914,522 B2 | 3/2011 | Morley et al. | |
| 7,950,306 B2 | 5/2011 | Stuart | |
| 7,967,742 B2 | 6/2011 | Hoeg et al. | |
| 7,987,001 B2 | 7/2011 | Teichman et al. | |
| 8,010,180 B2 | 8/2011 | Quaid et al. | |
| 8,287,522 B2 | 10/2012 | Moses et al. | |
| 8,343,048 B2 | 1/2013 | Warren, Jr. | |
| 8,442,621 B2 | 5/2013 | Gorek et al. | |
| 8,945,140 B2 | 2/2015 | Hubschman et al. | |
| 9,002,432 B2 | 4/2015 | Feilkas | |
| 9,119,655 B2 | 9/2015 | Bowling et al. | |
| 9,119,670 B2 | 9/2015 | Yang et al. | |
| 9,168,104 B2 | 10/2015 | Dein | |
| 9,381,085 B2 | 7/2016 | Axelson, Jr. et al. | |
| 9,480,534 B2 | 11/2016 | Bowling et al. | |
| 9,510,771 B1 | 12/2016 | Finley et al. | |
| 9,510,914 B2 | 12/2016 | Yang et al. | |
| 9,542,743 B2 | 1/2017 | Tenney et al. | |
| 9,566,052 B2 | 2/2017 | Novak | |
| 9,603,665 B2 | 3/2017 | Bowling et al. | |
| 9,615,987 B2 | 4/2017 | Worm et al. | |
| 9,629,595 B2 | 4/2017 | Walker et al. | |
| 9,642,606 B2 | 5/2017 | Charles et al. | |
| 9,707,043 B2 | 7/2017 | Bozung | |
| 9,901,408 B2 | 2/2018 | Larkin | |
| 9,901,409 B2 | 2/2018 | Yang et al. | |
| 10,039,474 B2 | 8/2018 | Taylor et al. | |
| 10,045,882 B2 | 8/2018 | Balicki et al. | |
| 10,064,691 B2 | 9/2018 | Frimer et al. | |
| 10,512,509 B2 | 12/2019 | Bowling et al. | |
| 2002/0035321 A1 | 3/2002 | Bucholz et al. | |
| 2002/0120188 A1* | 8/2002 | Brock | A61B 34/35 600/407 |
| 2003/0078470 A1 | 4/2003 | Borst et al. | |
| 2003/0125622 A1 | 7/2003 | Schweikard et al. | |
| 2003/0181800 A1 | 9/2003 | Bonutti | |
| 2003/0208296 A1 | 11/2003 | Brisson et al. | |
| 2004/0010190 A1 | 1/2004 | Shahidi | |
| 2004/0024311 A1* | 2/2004 | Quaid, III | A61B 90/39 600/428 |
| 2004/0034283 A1 | 2/2004 | Quaid | |
| 2004/0034302 A1 | 2/2004 | Abovitz et al. | |
| 2004/0059194 A1 | 3/2004 | Berg et al. | |
| 2004/0073279 A1 | 4/2004 | Malackowski et al. | |
| 2004/0077939 A1 | 4/2004 | Graumann | |
| 2004/0106916 A1 | 6/2004 | Quaid et al. | |
| 2004/0138556 A1 | 7/2004 | Cosman | |
| 2005/0054895 A1 | 3/2005 | Hoeg et al. | |
| 2005/0171553 A1 | 8/2005 | Schwarz et al. | |
| 2006/0020279 A1 | 1/2006 | Chauhan et al. | |
| 2006/0074299 A1* | 4/2006 | Sayeh | A61N 5/1049 600/426 |
| 2006/0109266 A1 | 5/2006 | Itkowitz et al. | |
| 2006/0142657 A1 | 6/2006 | Quaid et al. | |
| 2006/0155262 A1 | 7/2006 | Kishi et al. | |
| 2006/0176242 A1 | 8/2006 | Jaramaz et al. | |
| 2007/0260394 A1 | 11/2007 | Dean | |
| 2007/0265527 A1 | 11/2007 | Wohlgemuth | |
| 2007/0270685 A1 | 11/2007 | Kang et al. | |
| 2008/0021283 A1 | 1/2008 | Kuranda | |
| 2008/0058776 A1 | 3/2008 | Jo et al. | |
| 2008/0077158 A1 | 3/2008 | Haider et al. | |
| 2008/0108912 A1 | 5/2008 | Node-Langlois | |
| 2008/0161829 A1 | 7/2008 | Kang | |
| 2008/0212082 A1 | 9/2008 | Froggatt et al. | |
| 2008/0214898 A1 | 9/2008 | Warren | |
| 2008/0243142 A1 | 10/2008 | Gildenberg | |
| 2009/0003975 A1 | 1/2009 | Kuduvalli et al. | |
| 2009/0024140 A1 | 1/2009 | Allen et al. | |
| 2009/0157059 A1 | 6/2009 | Allen et al. | |
| 2010/0331859 A1 | 12/2010 | Omori | |
| 2011/0106102 A1 | 5/2011 | Balicki et al. | |
| 2011/0130761 A1 | 6/2011 | Plaskos et al. | |
| 2011/0152676 A1 | 6/2011 | Groszmann et al. | |
| 2011/0263971 A1 | 10/2011 | Nikou et al. | |
| 2011/0264107 A1 | 10/2011 | Nikou et al. | |
| 2012/0059378 A1 | 3/2012 | Farrell | |
| 2012/0071752 A1 | 3/2012 | Sewell et al. | |
| 2012/0071893 A1 | 3/2012 | Smith et al. | |
| 2012/0143084 A1 | 6/2012 | Shoham | |
| 2012/0330429 A1 | 12/2012 | Axelson, Jr. et al. | |
| 2013/0006267 A1 | 1/2013 | Odermatt et al. | |
| 2013/0019883 A1 | 1/2013 | Worm et al. | |
| 2013/0060278 A1 | 3/2013 | Bozung et al. | |
| 2013/0096574 A1 | 4/2013 | Kang et al. | |
| 2013/0169423 A1* | 7/2013 | Iorgulescu | G06F 3/016 340/407.1 |
| 2014/0005684 A1 | 1/2014 | Kim et al. | |
| 2014/0039681 A1 | 2/2014 | Bowling et al. | |
| 2014/0107426 A1 | 4/2014 | Wilson | |
| 2014/0171787 A1 | 6/2014 | Garbey et al. | |
| 2014/0180290 A1 | 6/2014 | Otto et al. | |
| 2015/0018622 A1 | 1/2015 | Tesar et al. | |
| 2015/0351860 A1 | 12/2015 | Piron et al. | |
| 2016/0113728 A1 | 4/2016 | Piron et al. | |
| 2016/0345917 A1 | 12/2016 | Daon et al. | |
| 2017/0143432 A1 | 5/2017 | Bowling et al. | |
| 2018/0153626 A1 | 6/2018 | Yang et al. | |
| 2020/0085513 A1 | 3/2020 | Bowling et al. | |

FOREIGN PATENT DOCUMENTS

| | | |
|---|---|---|
| JP | 2005532890 A | 11/2005 |
| JP | 2006106419 A | 4/2006 |
| KR | 20100098055 A | 9/2010 |
| KR | 20110036453 A | 4/2011 |
| WO | 9611624 A2 | 4/1996 |
| WO | 99037220 A1 | 7/1999 |
| WO | 0021450 A1 | 4/2000 |
| WO | 0035366 A1 | 6/2000 |
| WO | 0059397 A1 | 10/2000 |
| WO | 0060571 A1 | 10/2000 |
| WO | 200200131 A1 | 1/2002 |
| WO | 0224051 A2 | 3/2002 |
| WO | 02060653 A2 | 8/2002 |
| WO | 02065931 A1 | 8/2002 |
| WO | 02074500 A2 | 9/2002 |
| WO | 02076302 A2 | 10/2002 |
| WO | 03094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2006058633 A1 | 6/2006 |
| WO | 2006063156 A1 | 6/2006 |
| WO | 2006091494 A1 | 8/2006 |
| WO | 2006106419 A2 | 10/2006 |
| WO | 2007017642 A1 | 2/2007 |
| WO | 2007111749 A2 | 10/2007 |
| WO | 2007117297 A2 | 10/2007 |

(56) References Cited

FOREIGN PATENT DOCUMENTS

| WO | 2007136739 A2 | 11/2007 |
|---|---|---|
| WO | 2007136768 A2 | 11/2007 |
| WO | 2007136769 A2 | 11/2007 |
| WO | 2007136771 A2 | 11/2007 |
| WO | 2009059330 A2 | 5/2009 |
| WO | 2011021192 A1 | 2/2011 |
| WO | 2011088541 A1 | 7/2011 |
| WO | 2011106861 A1 | 9/2011 |
| WO | 2011113483 A1 | 9/2011 |
| WO | 2011128766 A2 | 10/2011 |
| WO | 2011133873 A1 | 10/2011 |
| WO | 2011133927 A2 | 10/2011 |
| WO | 2011134083 A1 | 11/2011 |
| WO | 2012018816 A2 | 2/2012 |
| WO | 2013132501 A1 | 9/2013 |
| WO | 2015100310 A1 | 7/2015 |

OTHER PUBLICATIONS

Kienzle, III, T.C. et al., "Total Knee Replacement Computer-assisted surgical system uses a calibrated robot", Engineering in Medicine and Biology, May 1995, pp. 301-306, vol. 14, Issue 3, IEEE; 35 pages.

Koseki, Y. et al., "Robotic assist for MR-guided surgery using leverage and parallelepiped mechanism", Medical Image Computing and Computer-Assisted Intervention—MICCAI 2000, Lecture Notes in Computer Science, 2000, pp. 940-948, vol. 1935, Springer Berlin Heidelberg; 9 pages.

Lavallee, S. et al., "Computer Assisted Spine Surgery a technique for accurate transpedicular screw fixation using CT data and a 3-D optical localizer", Journal of Image Guided Surgery, 1995, pp. 65-73; 9 pages.

Lea, J.T. et al., Registration and immobilization in robot-assisted surgery, Journal of Image Guided Surgery, Computer Aided Surgery, 1995, vol. 1, No. 2, pp. 80-87; 11 pages.

Lea, J.T. Registration Graphs a Language for Modeling and Analyzing Registration in Image-Guided Surgery, Dec. 1998, Evanston, Illinois, US; 49 pages.

Leitner, F. et al., Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.

Levison, T.J. et al., "Surgical Navigation for THR a Report on Clinical Trial Utilizing HipNav", MICCAI 2000, LNCS 1935, pp. 1185-1187, 2000, Springer-Verlag Berlin Heidelberg; 3 pages.

Louhisalmi, Y. et al., "Development of a Robotic Surgical Assistant", 1994, pp. 1043-1044, IEEE, Linnanmaa, Oulu, FI; 2 pages.

M. Fadda, T. Wang, M. Marcacci, S. Martelli, P. Dario, G. Marcenaro, M. Nanetti, C. Paggetti, A. Visani and S. Zaffagnini, Computer-Assisted Knee Arthroplasty at Rizzoli Institutes, First International Symposium on Medical Robotics and ComputerAssisted Surgery, Sep. 22-24, 1994, pp. 26-30, Pittsburgh, Pennsylvania, US; 6 pages.

M. Fadda; S. Martelli; P. Dario; M. Marcacci; S. Zaffagnini; A. Visani, Premiers Pas Vers La Dissectomie et la Realisation de Protheses du Genou a L'Aide de Robots, Innov. Tech. Bio. Med. , 1992, pp. 394-409, vol. 13, No. 4; 16 pages.

Machine-Assisted English language translation for WO 0021450 A1 extracted www.espacenet.com on Jul. 3, 2014; 28 pages.

Machine-Assisted English language translation for WO 0059397 A1 extracted www.espacenet.com Jul. 3, 2014; 33 pages.

Machine-Assisted English language translation for WO 02074500 extracted www.espacenet.com Apr. 30, 2014; 26 pages.

Matsen, F.A. et al., Robotic Assistance in Orthopaedic Surgery a Proof of Principle Using Distal Femoral Arthroplasty, Clinical Orthopaedic Related Research, Nov. 1993, pp. 178-186, vol. 296; 9 pages.

Nolte, L.P. et al., A Novel Approach to Computer Assisted Spine Surgery, Proc. First International Symposium on Medical Robotics and Computer Assisted Surgery, Pittsburgh, 1994, pp. 323-328; 7 pages.

O'Toole, R.V. et al., "Biomechanics for Preoperative Planning and Surgical Simulations in Orthopaedics", Computers in Biology and Medicine, Mar. 1995, pp. 183-191, vol. 25, Issue 2; 8 pages.

Orto Maquet and CASPAR: An Automated Cell for Prosthesis Surgery, Robotics World, Sep./Oct. 1999, pp. 30-31, Circular No. 87 on Reader Reply Card; 2 pages.

Paul, H.A. et al., A Surgical Robot for Total Hip Replacement Surgery, International Conference on Robotics and Automation, 1992, pp. 606-611, IEEE, Nice, FR; 6 pages.

Paul, H.A. et al., Robotic Execution of a Surgical Plan, Systems, Man and Cybernetics, 1992., IEEE International Conference on, Oct. 18-21, 1992,pp. 1621-1623, IEEE, Sacramento, California, US; 3 pages.

Preising, B. et al., A Literature Review Robots in Medicine, Engineering in Medicine and Biology Magazine, IEEE (vol. 10, Issue: 2), Jun. 1991, pp. 13-22, IEEE; 10 pages.

Prototype of Instrument for Minimally Invasive Surgery with 6-Axis Force Sensing CapabilityU. Seibold, B. Kubler, and G. Hirzinger, Prototype of Instrument for Minimally Invasive Surgery with 6-Axis Force Sensing Capability, Robotics and Automation, 2005. ICRA 2005. Proceedings of the 2005 IEEE International Conference on, Apr. 18-22, 2005, pp. 498-503, IEEE, Barcelona, Spain; 6 pages.

Quaid, A.E. et al., Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.

R.H. Taylor; C.B. Cutting; Y.-Y. Kim; A.D. Kalvin; D. Larose; B.Haddad; D. Khoramabadi; M. Noz; R. Olyha; N. Bruun; D. Grimm, A Model-Based Optimal Planning and Execution System with Active Sensing and Passive Manipulation for Augmentation of HumanPrecision in Computer-Integrated Surgery, Experimental Robotics II, The 2nd International Symposium, Lecture Notes in Control and Information Sciences, pp. 177-195, vol. 190, Springer Berlin Heidelberg, Toulouse, FR, Jun. 25-27, 1991; 19 pages.

R.H. Taylor; H. A. Paul; B.D. Mittelstadt; W. Hanson; P. Kazanzides; J. Zuhars; E. Glassman; B.L. Mustis; B. Williamson; W.L. Bargar, An Image-directed Robotic System for Hip Replacement Surgery, Oct. 1990, pp. 111-116, vol. 8, No. 5; 7 pages.

Raczkowsky, J. et al., "Ein Robotersystem fur craniomaxillofaciale chirurgische Eingriffe (A robotic system for surgical procedures craniomaxillofaciale)", with English language abstract, Computer Forsch. Entw., 1999, pp. 24-35, vol. 14, Springer-Verlag; 12 pages.

Rembold, U. et al., "Surgical Robotics: An Introduction", Journal of Intelligent and Robotic Systems vol. 30, No. 1, pp. 1-28, 2001, Kluwer Academic Publishers; 28 pages.

Rohling, R. et al., Comparison of Relative Accuracy Between a Mechanical and an Optical Position Tracker for Image-Guided Neurosurgery, Journal of Image Guided Surgery, 1995, pp. 30-34, vol. 1, No. 1; 4 pages.

S. Haßfeld; C. Burghart; I. Bertovic; J. Raczkowsky; H. Worn; U. Rembold; J. Muhling, Intraoperative Navigation Techniques Accuracy Tests and Clinical Report, In: Computer Assisted Radiology and Surgery (CARS'98), Tokyo, Jun. 1998, pp. 670-675, Elseview Science B.V.; 6 pages.

S.C. Ho; R.D. Hibberd; B.L. Davies, Robot Assisted Knee Surgery, IEEE Engineering in Medicine and Biology, May/Jun. 1995, pp. 292-300, vol. 14, No. 3; 9 pages.

Salisbury, J.K., Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.

Santos-Munne, Julio J. et al., "A Stereotactic/Robotic System for Pedicle Screw Placement", Interactive Technology and the New Paradigm for Healthcare, (Proceedings of theMedicine Meets Virtual Reality III Conference, San Diego, 1995), pp. 326-333, IOS Press and Ohmsha; 8 pages.

Schmidt, T. et al., "EasyGuide Neuro, A New System for Image-Guided Planning", Simulation and Navigation in Neurosurgery, Biomedical Engineering, vol. 40, Supplement 1, 1995, pp. 233-234, Hamburg, DE; 2 pages, and partial English language translation of EasyGuide Neuro, A New System for Image-Guided Planning, Simulation and Navigation in Neurosurgery, 1 page.

(56) References Cited

OTHER PUBLICATIONS

Shinsuk, P., Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.
Sim, C. et al., Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.
Simon, D.A. et al., Accuracy validation in image-guided orthopaedic surgery, In Medical Robotics and Computer Assisted Surgery, 1995, pp. 185-192, Wiley; 8 pages.
Spencer, E.H., The ROBODOC Clinical Trial A Robotic Assistant for Total Hip Arthroplasty, Orthopaedic Nursing, Jan.-Feb. 1996, pp. 9-14, vol. 15, Issue 1; 6 pages.
Spetzger, U. et al., "Frameless Neuronavigation in Modern Neurosurgery", Minimally Invasive Neurosurgery, Dec. 1995, pp. 163-166, vol. 38; 4 pages.
T. Wang; M. Fadda; M. Marcacci; S. Martelli; P. Dario; A. Visani, A robotized surgeon assistant, Intelligent Robots and Systems '94. 'Advanced Robotic Systems and the Real World', IROS '94. Proceedings of the IEEE/RSJ/GI International Conference on, Sep. 12-16, 1994, pp. 862-869, vol. 2, IEEE, Munich, Germany, 8 pages.
T.C. Kienzle, III; S.D. Stulberg; M. Peshkin; A. Quaid; C.-H. Wu, An Integrated CAD-Robotics System for Total Knee Replacement Surgery, Systems, Man and Cybernetics, 1992., IEEE International Conference on, Oct. 18-21, 1992, pp. 1609-1614, vol. 2,IEEE, Chicago, IL, USA; 6 pages.
Taylor, R. et al., A Steady-Hand Robotic System for Microsurgical Augementation, MICCA199: the Second International Conference on Medical ImageComputing and Computer-Assisted Intervention, Cambridge, England, Sep. 19-22, 1999. MICCAI99 Submission #1361999, pp. 1031-1041, Springer-Verlag Berlin Heidelberg; 11 pages.
Taylor, R.H. et al., An Image-Directed Robotic System for Precise Orthopaedic Surgery, Robotics and Automation, IEEE Transactions on, Jun. 1994, pp. 261-275, vol. 10, Issue 3, IEEE; 15 pages.
Tonet, O. et al., An Augmented Reality Navigation System for Computer Assisted Arthroscopic Surgery of the Knee, Medical Image Computing and Computer-AssistedIntervention—MICCAI 2000, Lecture Notes in Computer Science, 2000, pp. 1158-1162, vol. 1935, Springer Berlin Heidelberg; 5 pages.
Troccaz, J. et al., A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.
Troccaz, J. et al., Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages.
Troccaz, J. et al., Guiding systems for computer-assisted surgery introducing synergistic devices and discussing the different approaches, Medical Image Analysis, Jun. 1998, vol. 2, No. 2, pp. 101-119, Elsevier B.V.; 19 pages.
U.S. Appl. No. 61/679,258, filed Aug. 3, 2012.
U.S. Appl. No. 61/753,219, filed Jan. 16, 2013.
Van Ham, G. et al., Accuracy study on the registration of the tibia by means of an intramedullary rod in robot-assisted total knee arthroplasty, PosterSession—Knee Arthroplasty—Valencia Foyer, 46th Annual Meeting, Orthopaedic Research Society, Mar. 12-15, 2000, Orlando, Florida, Jan. 1, 2010, p. 450; 1 page.
Van Ham, G. et al., Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.
W. Siebert; S. Mai; R. Kober; P.F. Heeckt, Technique and first clinical results of robot-assisted total knee replacement, The Knee, Sep. 2002, pp. 173-180, vol. 9, Issue 3, Elsevier B.V.; 8 pages.

Watanable, E. et al., "Three-Dimensional Digitizer (Neuronavigator)—New Equipment for Computed Tomography-Guided Stereotaxic Surgery", Surgical Neurology, Jun. 1987, pp. 543-547, vol. 27, Issue 6, ElsevierInc.; 5 pages.
Yoshimine, Kato A. et al., "A frameless, armless navigational system for computer-assisted neurosurgery", Technical note, Journal of Neurosurgery, vol. 74, May 1991, pp. 845-849; 5 pages.
A.M. Digioia, III; B. Jaramaz; B. D. Colgan, Computer Assisted Orthopaedic Surgery Image Guided and Robotic Assistive Technologies, Clinical Orthopaedics & Related Research:. Sep. 1998, pp. 8-16, vol. 354, Lippincott Williams & Wilkins, Pittsburgh,PA, USA; 9 pages.
Abovitz, R., Digital surgery the future of medicine and human-robot symbiotic interaction, Industrial Robot: An International Journal, 2001, pp. 401-406, vol. 28, Issue 5, Hollywood, FL, USA; 5 pages.
Abovitz, R.A., "Human-Interactive Medical Robotics", Abstract for CAOS 2000, 2000, pp. 71-72; 2 pages.
Ansara,. D. et al., Visual and haptic collaborative tele-presence, Computers & Graphics, 2001, pp. 789-798, vol. 25, Elsevier, Inc.; 10 pages.
B.L. Davies, Robotics in minimally invasive surgery, Through the Keyhole: Microengineering in Minimally Invasive Surgery, IEE Colloquium on, Jun. 6, 1995, p. 5/1-5/2, London, UK; 2 pages.
Bainville, E. et al., "Concepts and Methods of Registration for Computer-Integrated Surgery", Computer Assisted Orthopedic Surgery (CAOS), 1999, pp. 15-34, Hogrefe & Huber Publishers, Bern; 22 pages.
Bargar, W.L. et al., "Primary and Revision Total Hip Replacement Using the Robodoc System", Clinical Orthopaedics and Related Research, Sep. 1998, pp. 82-91, No. 354; 10 pages.
Bouazza-Marouf, K. et al., "Robot-assisted invasive orthopaedic surgery", Mechatronics in Surgery, Jun. 1996, pp. 381-397, vol. 6, Issue 4, UK; 17 pages.
Brandt, G. et al., "CRIGOS: A Compact Robot for Image-Guided Orthopedic Surgery," Information Technology in Biomedicine, IEEE Transactions on, vol. 3, No. 4, pp. 252-260, Dec. 1999; 9 pages.
Brisson, G. et al., Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-VerlagBerlin Heidelberg 2004; 8 pages.
Buckingham, R.O., "Robotics in surgery a new generation of surgical tools incorporate computer technology and mechanical actuation to give surgeons much finer control than previously possible during some operations", IEE Review, Sep. 1994, pp. 193-196; 4 pages.
Buckingham, R.O., "Safe Active Robotic Devices for Surgery, Systems, Man and Cybernetics", 1993. 'Systems Engineering in the Service of Humans', Conference Proceedings., International Conference on, Oct. 17-20, 1993, pp. 355-358, vol. 5, IEEE, LeTougeut; 4 pages.
Burghart, C.R. et al., A. Pernozzoli; H. Grabowski; J. Muenchenberg; J. Albers; S. Hafeld; C. Vahl; U. Rembold; H. Woern, Robot assisted craniofacial surgery first clinical evaluation, Computer Assisted Radiology andSurgery, 1999, pp. 828-833; 7 pages.
Burghart, C.R. et al., "Robot Controlled Osteotomy in Craniofacial Surgery", First International Workshop on Haptic Devices in Medical Applications Proceedings, Jun. 23, 1999, pp. 12-22, Paris, FR; 13 pages.
Burghart, C.R., "Robotergestutzte Osteotomie in der craniofacialen Chirurgie (Robot Clipped osteotomy in craniofacial surgery)", Jul. 1, 1999, GCA-Verlag, 2000; 250 pages.
C. Doignon; F. Nageotte; M. De Mathelin, Segmentation and guidance of multiple rigid objects for intra-operative endoscopic vision, Proceeding WDV'05/WDV'06/ICCV'05/ECCV'06 Proceedings of the 2005/2006 International Conference on Dynamical Vision,2006, pp. 314-327, Springer-Verlag Berlin, Heidelberg, Illkirch, FR; 14 pages.
C. Meng; T. Wang; W. Chou; S. Luan; Y. Zhang; Z. Tian, Remote surgery case robot-assisted teleneurosurgery, Robotics and Automation, 2004. Proceedings. ICRA '04. 2004 IEEE International Conference on, Apr. 26-May 1, 2004, pp. 819-823, vol. 1, IEEE, New Orleans, LA, USA; 5 pages.

(56) References Cited

OTHER PUBLICATIONS

C.B. Zilles; J.K. Salisbury, A Constraint-Based God-object Method for Haptic Display, Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.
C.N. Riviere and N.V. Thakor, Modeling and Canceling Tremor in Human-Machine Interfaces, Engineering in Medicine and Biology Magazine, IEEE, vol. 15, Issue 3, May/Jun. 1996, pp. 29-36, IEEE; 8 pages.
C.O.R. Grueneis; R.J. Richter; F.F. Hennig, Clinical Introduction of the Caspar System Problems and Initial Results, 4th International Symposium of Computer Assited Orthopaedic Surgery, CAOS'99, Abstracts from CAOS '99, 1999, p. 160, Davos, Switzerland; 1 pages.
Choi, D.Y. et al., "Flexure-based Manipulator for Active Handheld Microsurgical Instrument", Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005; 4 pages.
Colgate, J.E. et al., "Issues in the Haptic Display of Tool Use", Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.
Davies, B.L. et al., Acrobot-using robots and surgeons synergistically in knee surgery, Advanced Robotics, 1997. ICAR '97. Proceedings., 8th International Conference on, Jul. 7-9, 1997, pp. 173-178, IEEE, Monterey, CA, USA; 6 pages.
Davies, B.L. et al., Active compliance in robotic surgery—the use of force control as a dynamic constraint, Proceedings of the Institution of Mechanical Engineers, Part H: Journal of Engineeringin Medicine, Apr. 1, 1997, pp. 285-292, vol. 211, Sage; 9 pages.
Davies, B.L. et al., Neurobot a special-purpose robot for neurosurgery, Robotics and Automation, 2000. Proceedings. ICRA '00. IEEE International Conference on, Apr. 2000, pp. 4103-4108, vol. 4, IEEE, San Francisco, CA, USA; 6 pages.
Davies, B.L., "A review of robotics in surgery", Proceedings of the Institution of Mechanical Engineers, Part H: Journal of Engineering in Medicine Jan. 1, 2000, vol. 214, No. 1, pp. 129-140, Sage Publications; 13 pages.
Davies, B.L., "Computer-assisted and robotics surgery", International Congress and Symposium Series 223, 1997, pp. 71-82, Royal Society of Medicine Press Limited; 12 pages.
Delp, S.L. et al., "Computer Assisted Knee Replacement", Clinical Orthopaedics, Sep. 1998, pp. 49-56, vol. 354, Lippincott-Raven Publishers; 8 pages.
Ellis, R.E. et al., "A surgical planning and guidance system for high tibial osteotomy", Computer Aided Surgery, Apr. 16, 1999, 264-274, vol. 4, Wiley-Liss, Inc.; 11 pages.
Engel, D. et al., A Safe Robot System for Craniofacial Surgery, Robotics and Automation, 2001. Proceedings 2001 ICRA. IEEE International Conference on (vol. 2), pp. 2020-2024, IEEE; 5 pages.
English language abstract and machine-assisted English translation for KR 2010-0098055 extracted from espacenet.com database on Jun. 27, 2019, 14 pages.
English language abstract and machine-assisted English translation for KR 2011-0036453 extracted from espacenet.com database on Jun. 27, 2019, 31 pages.

English language abstract for CN 101254103 extracted from espacenet. com database on Sep. 25, 2017, 2 pages.
English language abstract for JP 2005-532890 extracted from espacenet. com database on Feb. 8, 2018, 1 page.
English language abstract for JP 2006-106419 extracted from espacenet. com database on Feb. 8, 2018, 1 page.
Fadda, M. et al., "Computer Assisted Planning for Total Knee Arthroplasty", 1997, pp. 619-628; 10 pages.
Fluete, M. et al., "Incorporating a statistically based shape model into a system for computer-assisted anterior cruciate ligament surgery", Medical Image Analysis, Oct. 1999, pp. 209-222, vol. 3, No. 3, FR; 14 pages.
H.A. Paul; W.L. Bargar; B. Mittlestadt; B. Musits; R. H. Taylor; P. Kazanzides; J. Zuhars; B. Williamson; W. Hanson, Development of a Surgical Robot for Cementless Total Hip Arthroplasty, Clinical Orthopaedics and Related Research, Dec. 1992, pp. 57-66, No. 285, Sacramento, CA, USA; 10 pages.
Haider, H. et al., Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.
Harris, S.J. et al., "Experiences with Robotic Systems for Knee Surgery", CVRMed-MRCAS'97, Lecture Notes in Computer Science, 1997, pp. 757-766, vol. 1205, Springer Berlin Heidelberg, London, UK; 10 pages.
Harris, S.J. et al., "Intra-operative Application of a Robotic Knee Surgery System", Medical Image Computing and Computer-Assisted Intervention—MICCAI'99, 1999, pp. 1116-1124, vol. 1679, Springer-Verlag Berlin Heidelberg; 9pages.
Ho, S.C. et al., Force Control for Robotic Surgery, ICAR '95, 1995, pp. 21-32, London, UK; 12 pages.
Hyosig, K. et al., "Autonomous Suturing using Minimally Invasive Surgical Robots" Control Applications, Sep. 25-27, 2000. Proceedings of the 2000 IEEE International Conference on, 2000, pp. 742-747, IEEE, Anchorage, AK, USA; 6 pages.
Hyosig, K. et al., "EndoBot A Robotic Assistant in Minimally Invasive Surgeries", Robotics and Automation, 2001. Proceedings 2001 ICRA. IEEE International Conference on, Seoul, KR, 2001, pp. 2031-2036, vol. 2, IEEE, Troy, NY, USA; 6 pages.
International Search Report for Application No. PCT/US2014/024269 dated Oct. 17, 2014, 6 pages.
J L. Moctezuma, F. Gosse and H.-J. Schulz, A Computer and Robotic Aided Surgery System for Accomplishing Osteotomies, First International Symposium onMedical Robotics and Computer Assisted Surgery, Sep. 22-24, 1994, Pittsburgh, Pennsylvania, US; 6 pages.
J. Andreas Breientzen, Octree-based Volume Sculpting, Proc. Late Breaking Hot Topics, IEEE Visualization '98, pp. 9-12, 1998; 4 pages.
Jakopec, M. et al., The first clinical application of a "hands-on" robotic knee surgery system, Computer Aided Surgery , 2001, pp. 329-339, vol. 6, Issue 6, Wiley-Liss, Inc.; 11 pages.
Jaramaz, B. et al., Range of Motion After Total Hip Arthroplasty Experimental Verification of the Analytical Simulator, CVRMed-MRCAS'97, Lecture Notes in Computer Science, Feb. 20, 1997, pp. 573-582, vol. 1205,Springer Berlin Heidelberg, Pittsburgh, PA, USA; 14 pages.
Kazanzides, P. et al., "Architecture of a Surgical Robot", Systems, Man and Cybernetics, 1992., IEEE International Conference on, Oct. 18-21, 1992, pp. 1624-1629, vol. 2, IEEE, Chicago, IL, USA; 6 pages.

* cited by examiner

SYSTEMS AND METHODS FOR ESTABLISHING VIRTUAL CONSTRAINT BOUNDARIES

RELATED APPLICATIONS

This application is continuation of U.S. patent application Ser. No. 16/685,442, filed Nov. 15, 2019, which is a continuation of U.S. patent application Ser. No. 15/416,717, filed Jan. 26, 2017, now U.S. Pat. No. 10,512,509, which is a division of U.S. patent application Ser. No. 14/205,702 filed on Mar. 12, 2014, now U.S. Pat. No. 9,603,665, which claims the benefit of U.S. Provisional Patent App. No. 61/780,148, filed on Mar. 13, 2013, the contents of each of the above-referenced applications being hereby incorporated by reference in their entirety.

TECHNICAL FIELD

The present disclosure relates generally to systems and methods for establishing and tracking virtual boundaries.

BACKGROUND

In robotic surgery virtual boundaries are created using computer aided design software to delineate areas in which an end effector of a robotic system can maneuver from areas in which the end effector is restricted. For instance, in orthopedic surgery a virtual cutting boundary may be created to delineate sections of bone to be removed by the end effector during the surgery from sections of bone that are to remain after the surgery.

A navigation system tracks movement of the end effector with respect to the virtual cutting boundary to determine a position and/or orientation of the end effector relative to the virtual cutting boundary. The robotic system cooperates with the navigation system to guide movement of the end effector so that the end effector does not move beyond the virtual cutting boundary.

Typically, virtual cutting boundaries are created prior to surgery. Virtual cutting boundaries are often created in a model of a patient's bone and fixed with respect to the bone so that when the model is loaded into the navigation system, the navigation system can track movement of the virtual cutting boundary by tracking movement of the bone.

Virtual boundaries may define other anatomical features to be avoided by the end effector during surgery. Such features include nerves or other types of tissue to be protected from contact with the end effector. Virtual boundaries are also used to provide virtual pathways that direct the end effector toward the anatomy being treated. These examples of virtual boundaries are often fixed in relationship to the anatomy being treated so that all of the boundaries are tracked together as the anatomy moves. However, some anatomical features or other objects in the operating room may move relative to the anatomy being treated. For instance, retractors used to provide an opening in tissue for the end effector may move relative to the anatomy being treated. If not accurately tracked using an appropriate dynamic virtual constraint boundary, the end effector may inadvertently strike the retractors. As a result, the end effector may be damaged or become inoperative and the retractor may become dislodged from its position.

Other typically untracked objects may also be in proximity to the end effector that should be avoided by the end effector, yet move relative to the anatomy being treated. Therefore, there is a need in the art for systems and methods for creating dynamic virtual boundaries for such objects.

SUMMARY

According to a first aspect, a surgical system is provided comprising: a robotic manipulator; a surgical instrument coupled to the robotic manipulator and being moveable by the robotic manipulator; a navigation system configured to track each of a first object, a second object, and the surgical instrument, wherein the first object is moveable relative to the second object; and one or more controllers configured to: associate a first virtual boundary with the first object; associate a second virtual boundary with the second object, wherein the first virtual boundary is moveable in relation to the second virtual boundary; control the robotic manipulator in relation to the first virtual boundary to facilitate interaction of the surgical instrument with the first object; and control the robotic manipulator in relation to the second virtual boundary to avoid interaction of the surgical instrument with the second object.

According to a second aspect, a method is provided of operating a surgical system, the surgical system comprising one or more controllers, a robotic manipulator, a surgical instrument coupled to the robotic manipulator and being moveable by the robotic manipulator, a navigation system configured to track each of a first object, a second object, and the surgical instrument, wherein the first object is moveable relative to the second object, the method comprising the one or more controllers: associating a first virtual boundary with the first object; associating a second virtual boundary with the second object, wherein the first virtual boundary is moveable in relation to the second virtual boundary; controlling the robotic manipulator in relation to the first virtual boundary for facilitating interaction of the surgical instrument with the first object; and controlling the robotic manipulator in relation to the second virtual boundary for avoiding interaction of the surgical instrument with the second object.

According to a third aspect, A non-transitory computer readable medium configured for a surgical system, the surgical system comprising one or more controllers, a robotic manipulator, a surgical instrument coupled to the robotic manipulator and being moveable by the robotic manipulator, a navigation system configured to track each of a first object, a second object, and the surgical instrument, wherein the first object is moveable relative to the second object, the non-transitory computer readable medium comprising instructions, which when executed by the one or more controllers, are configured to: associate a first virtual boundary with the first object; associate a second virtual boundary with the second object, wherein the first virtual boundary is moveable in relation to the second virtual boundary; control the robotic manipulator in relation to the first virtual boundary to facilitate interaction of the surgical instrument with the first object; and control the robotic manipulator in relation to the second virtual boundary to avoid interaction of the surgical instrument with the second object.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
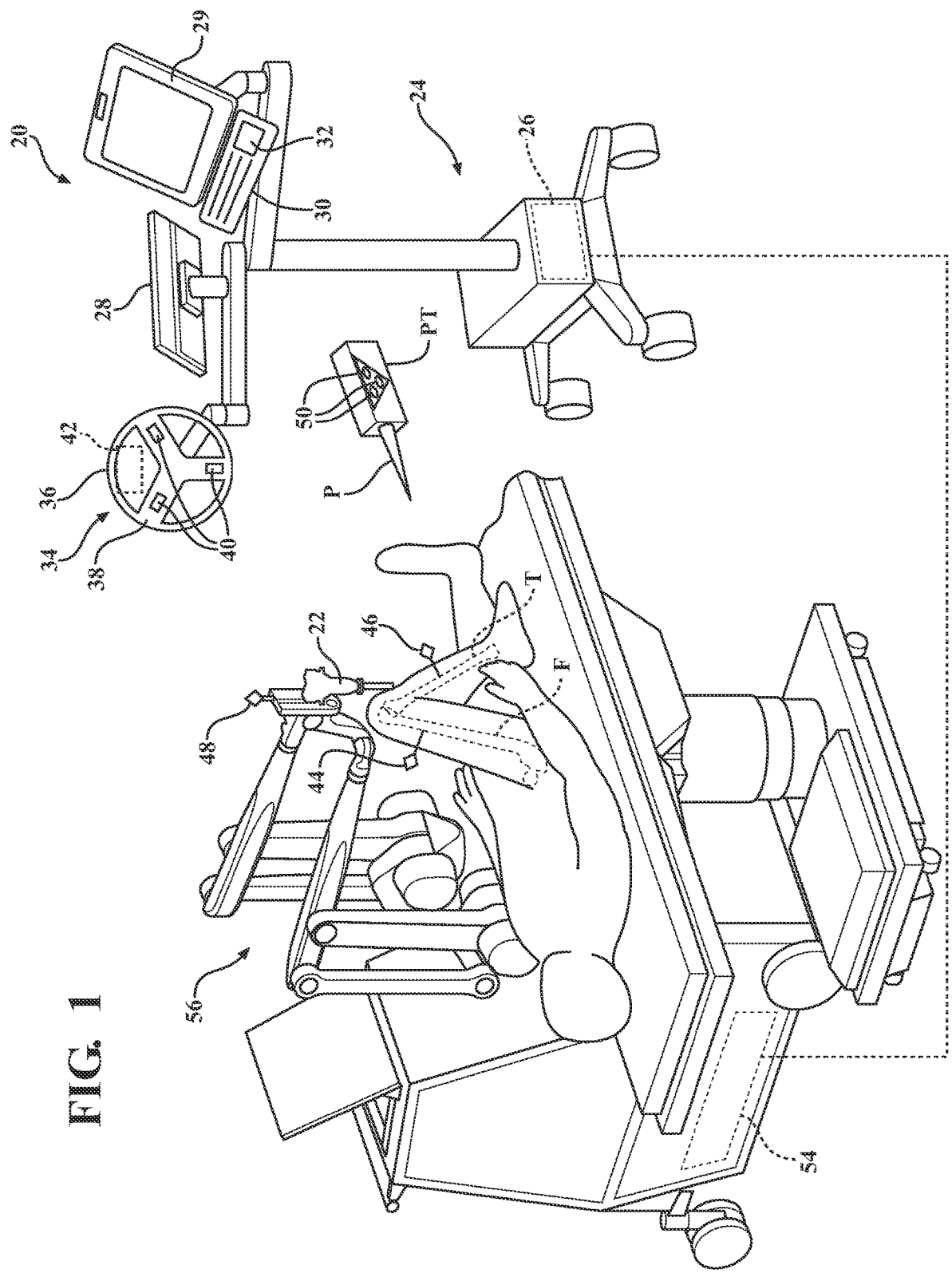
FIG. 1 is a perspective view of a navigation system of the present invention being used in conjunction with a robotic system.

Referring to FIG. 1 a surgical navigation system 20 is illustrated. The system 20 is shown in a surgical setting such as an operating room of a medical facility. The navigation system 20 is set up to track movement of various objects in the operating room. Such objects include, for example, a surgical instrument 22, a femur F of a patient, and a tibia T of the patient. The navigation system 20 tracks these objects for purposes of displaying their relative positions and orientations to the surgeon and, in some cases, for purposes of controlling or constraining movement of the surgical instrument 22 relative to virtual cutting boundaries associated with the femur F and tibia T.

The surgical navigation system 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices 30, 32 such as a keyboard and mouse can be used to input information into the navigation computer 26 or otherwise select/control certain aspects of the navigation computer 26. Other input devices are contemplated including a touch screen (not shown) or voice-activation.

A localizer 34 communicates with the navigation computer 26. In the embodiment shown, the localizer 34 is an optical localizer and includes a camera unit 36 (one example of a sensing device). The camera unit 36 has an outer casing 38 that houses one or more optical position sensors 40. In some embodiments at least two optical sensors 40 are employed, preferably three. The optical sensors 40 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field of view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System", hereby incorporated by reference.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Navigation system 20 includes a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. Provisional Patent Application No. 61/753,219, filed on Jan. 16, 2013, entitled, "Tracking Devices and Navigation Systems and Methods for Use Thereof", hereby incorporated by reference herein. In additional embodiments, a tracker (not shown) is attached to the patella to track a position and orientation of the patella. In yet further embodiments, the trackers 44, 46 could be mounted to other tissue types or parts of the anatomy.

An instrument tracker 48 is firmly attached to the surgical instrument 22. The instrument tracker 48 may be integrated into the surgical instrument 22 during manufacture or may be separately mounted to the surgical instrument 22 in preparation for the surgical procedures. The working end of the surgical instrument 22, which is being tracked by virtue of the instrument tracker 48, may be a rotating bur, electrical ablation device, or the like.

The trackers 44, 46, 48 can be battery powered with an internal battery or may have leads to receive power through the navigation computer 26, which, like the camera unit 36, preferably receives external power.

In the embodiment shown, the surgical instrument 22 is attached to a surgical manipulator. Such an arrangement is shown in U.S. patent application Ser. No. 13/958,070, entitled, "Surgical Manipulator Capable of Controlling a Surgical Instrument in Multiple Modes", the disclosure of which is hereby incorporated by reference.

In other embodiments, the surgical instrument 22 may be manually positioned by only the hand of the user, without the aid of any cutting guide, jig, or other constraining mechanism such as a manipulator or robot. Such a surgical instrument is described in U.S. patent application Ser. No. 13/600,888, filed Aug. 31, 2012, entitled, "Surgical Instrument Including Housing, a Cutting Accessory that Extends from the Housing and Actuators that Establish the Position of the Cutting Accessory Relative to the Housing", hereby incorporated by reference.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Figure 2:
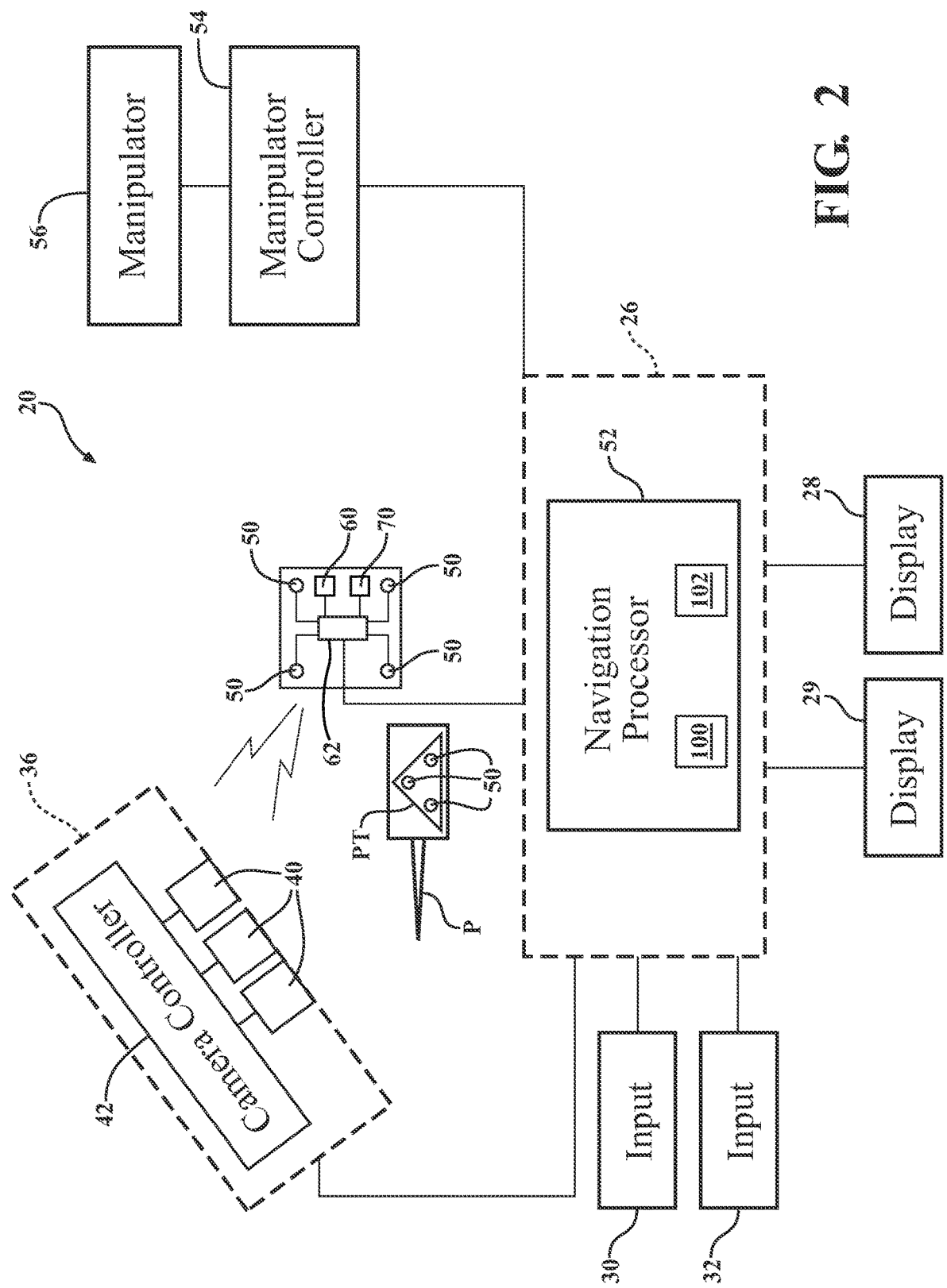
FIG. 2 is a schematic view of the navigation system.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor 60 and accelerometer 70, such as the trackers shown in U.S. Provisional Patent Application No. 61/753,219, filed on Jan. 16, 2013, entitled, "Tracking Devices and Navigation Systems and Methods for Use Thereof", hereby incorporated by reference.

The navigation computer 26 includes a navigation processor 52. It should be understood that the navigation processor 52 could include one or more processors to control operation of the navigation computer 26. The processors can be any type of microprocessor or multi-processor system. The term processor is not intended to limit the scope of the invention to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, navigation processor 52 determines the position of the working end of the surgical instrument 22 and the orientation of the surgical instrument 22 relative to the tissue against which the working end is to be applied. In some embodiments, navigation processor 52 forwards these data to a manipulator controller 54. The manipulator controller 54 can then use the data to control a robotic manipulator 56 as described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference.

The navigation processor 52 also generates image signals that indicate the relative position of the surgical instrument working end to the tissue. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen or other input/output device that allows entry of commands.

Figure 3:
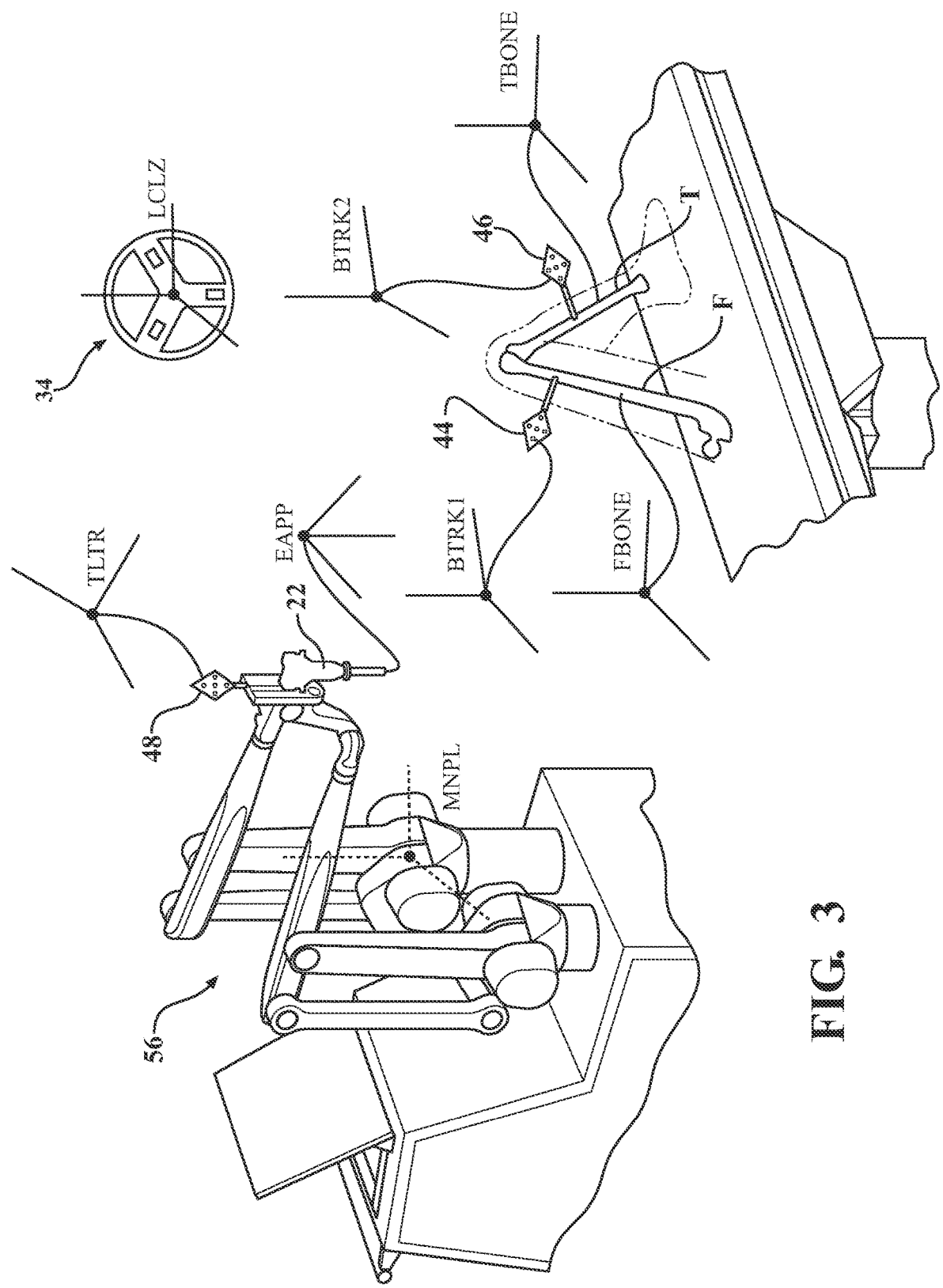
FIG. 3 is schematic view of the coordinate systems used in the navigation system.

Referring to FIG. 3, tracking of objects is generally conducted with reference to a localizer coordinate system LCLZ. The localizer coordinate system has an origin and an orientation (a set of x-, y-, and z-axes). During the procedure one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from localizer coordinate system LCLZ. Components of the navigation system 20 that have their own coordinate systems are the bone trackers 44, 46 and the instrument tracker 48. These coordinate systems are represented as, respectively, bone tracker coordinate systems BTRK1, BTRK2, and instrument tracker coordinate system TLTR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TB ONE using well known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIGS. 1 and 2), such as disclosed in U.S. Pat. No. 7,725,162 to Malackowski, et al., hereby incorporated by reference, having its own tracker PT (see FIG. 2), may be used to register the femur coordinate system FBONE and tibia coordinate system TB ONE to the bone tracker coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 44, 46. This pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

Referring to FIG. 2, a localization engine 100 is a software module that can be considered part of the navigation system 20. Components of the localization engine 100 run on navigation processor 52. In some versions of the invention, the localization engine 100 may run on the manipulator controller 54.

Localization engine 100 receives as inputs the optically-based signals from the camera controller 42 and, in some embodiments, the non-optically based signals from the tracker controller 62. Based on these signals, localization engine 100 determines the pose of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the bone trackers 44, 46. Coordinate transformer 102 also stores the data indicating the pose of the working end of the surgical instrument relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, PHONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical instrument 22.

Before using the surgical instrument 22 to treat the patient, certain preparations are necessary such as draping the patient and preparing the surgical site for treatment. For instance, in knee arthroplasty, surgical personnel may secure the leg of interest in a leg holder, and drape the patient and equipment. One such leg holder is shown in U.S. patent application Ser. No. 13/554,010, entitled, "Multi-position Limb Holder", published as U.S. Patent Application Publication No. 2013/0019883, hereby incorporated by reference.

Other preparations include placing objects needed for surgery in the operating room. Some of these objects are used in proximity to areas in which the surgical instrument 22 will maneuver. These objects can include leg holders, retractors, suction/irrigation tools, surgical personnel, and the like. During the surgery, these objects are to be avoided by the surgical instrument 22. To facilitate the avoidance of these objects during the surgery position information for one or more of these objects is determined either directly or indirectly. In some embodiments, one or more of the objects are dynamically tracked by the navigation system 20 during the surgery.

Figure 4:
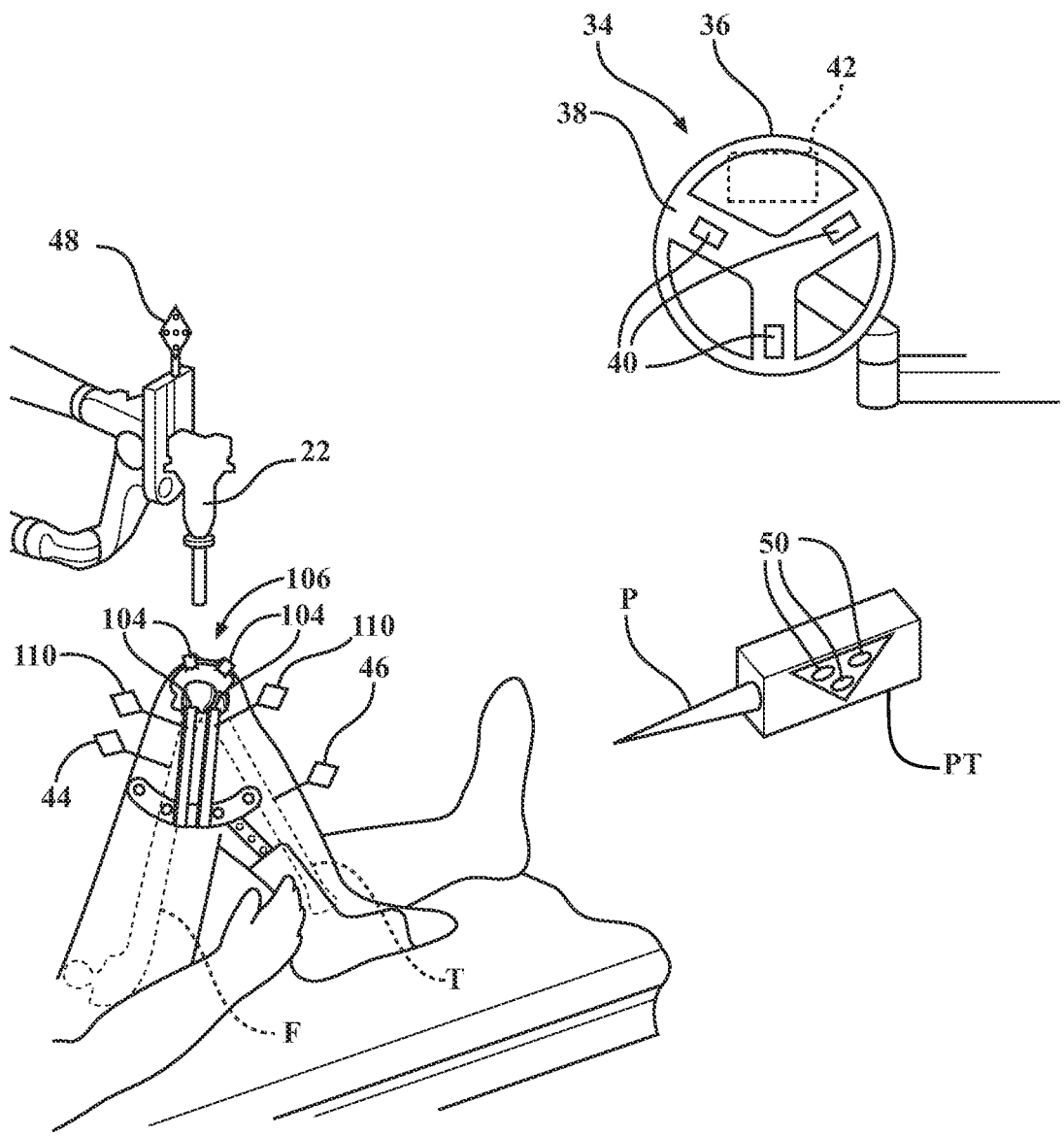
FIG. 4 is a perspective view of a tissue opening for accessing a knee joint by an end effector of the robotic system.

Referring to FIG. 4, in one embodiment, position information can be obtained indirectly from an object using the pointer instrument P, an example of which is disclosed in U.S. Pat. No. 7,725,162 to Malackowski, et al., hereby incorporated by reference. The pointer P has its own tracker PT with LEDs 50 that transmit signals to the camera unit 36 in the same manner as trackers 44, 46, 48. Position of a tip of the pointer P is known relative to the LEDs 50 on the pointer P and stored in the pointer P in electronic format for later transmitting to the camera unit 36 via transceivers. Alternatively, the position information for the tip is stored in the navigation computer 26 or calibrated to a known location in the field. In either case, since the tip position is known, the pointer P can be used to determine the positions of objects to be avoided by the surgical instrument 22.

Once the tip touches certain surfaces of the object, a trigger or switch (not shown) on the pointer P is actuated by the user or alternatively the tip may include a sensor that automatically senses when it is in contact with a surface. A corresponding signal is sent to the transceiver on the camera unit 36 to read the signals from the LEDs 50 on the pointer tracker PT so that the position of the tip can be calculated, which correlates to a point on the surface of the object. As more points on the surface are touched by the tip and their positions calculated by the navigation system 20, models of the object can be created to define a position and orientation of the object in the localizer coordinate system LCLZ. Such models can be created using conventional surface mapping tools and the like.

The created models are used as virtual constraint boundaries to guide movement of the surgical instrument 22. The models may be displayed on displays 28, 29 to show the locations of the objects and/or information relating to the models can be forwarded to the manipulator controller 54 to guide the manipulator 56 and corresponding movement of the surgical instrument 22 relative to these virtual constraint boundaries to prevent the object from being contacted by the surgical instrument 22.

When the object is stationary during the surgery the above method of determining position and/or orientation is suitable to provide a virtual constraint boundary, or if the object to be tracked is not stationary, but in a fixed location relative to another tracked object. However, if the object typically moves during the surgery, additional measures are needed to enable continuous tracking of the object. In some embodiments, mountable trackers 110 may be mounted to the objects. These trackers 110 may be generic with respect to the objects and thus, not be calibrated to the objects. In this case, the trackers 110 are first attached to the objects.

One such object may be a retractor, such as the retractor assemblies 104 shown in FIG. 4. The trackers 110 may be attached to the retractor assemblies 104 by a tracker connector located on the retractor assemblies 104, such as those shown in U.S. Pat. No. 7,725,162 to Malackowski, et al., hereby incorporated by reference, or the trackers 110 may be mounted with conventional fasteners or clamps to fix the trackers 110 to the retractor assemblies 104. Examples of retractor assemblies that may be used are shown in U.S. patent application Ser. No. 13/554,010, entitled, "Multi-position Limb Holder", published as U.S. Patent Application Publication No. 2013/0019883, hereby incorporated by reference. Once the tracker 110 is fixed to the retractor assembly 104, the pointer P can be used to register the surfaces or other points on the retractor assembly 104. Each tracker 110 includes three or more LEDs (not shown) that transmit signals to the camera unit 36 in the same manner as trackers 44, 46, 48. The camera unit 36 and/or navigation computer 26 are then able to determine a position of each of the LEDs in the localizer coordinate system LCLZ. While the camera unit 36 is receiving signals from the LEDs on tracker 110, the pointer P is used to touch on several points on the retractor assembly 104 and transmit corresponding signals to the camera unit 36 to determine position information from the pointer P using the pointer tracker PT. This enables the navigation computer 26 to associate points on the retractor assembly 104 with positions of the LEDs on the tracker 110. Then, through a boundary creation software module (not shown) run by the navigation processor 52, a virtual constraint boundary can be created that is associated with the retractor assembly 104 and dynamically trackable via the tracker 110.

In some embodiments, the boundary can be created by connecting each of the captured points together. This creates a web or mesh that defines a surface boundary. If only two points are captured, the boundary may be a line between the points. If three points are captured, the boundary may be a triangle formed by lines connecting adjacent points. The displays 28, 29 can be used to provide visual feedback of the shape of the boundary created. The input devices, e.g., mouse, touch screen, etc. could be used to modify the boundary such as by shifting the boundary, enlarging or shrinking the boundary, changing the shape of the boundary, etc. Once created, the boundary may be defined in the boundary creation software module as a virtual constraint boundary across which the surgical instrument 22 is prevented from moving in accordance with the robotic control functionality described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The manipulator controller 54 may also continuously track movement of the virtual constraint boundary and continuously adjust a path and/or orientation of the surgical instrument 22 as the virtual constraint boundary moves, to avoid the virtual constraint boundary.

The virtual constraint boundary can also be tracked simultaneously with tracking of a virtual cutting boundary associated with the femur F or tibia T described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The virtual constraint boundary may move relative to the virtual cutting boundary during the surgery. Tracking of the boundaries would also enable tracking of the relative movement between such boundaries.

Models of the objects being tracked may be displayed on displays 28, 29 to show the location of the objects. Representations of the virtual boundaries and the anatomy being treated may also be shown on displays 28, 29. Additionally, information relating to the virtual constraint boundaries and virtual cutting boundary can be forwarded to the manipulator controller 54 to guide the manipulator 56 and corresponding movement of the surgical instrument 22 relative to these virtual boundaries so that the surgical instrument 22 does not intrude on the virtual boundaries.

In some embodiments, a virtual boundary is associated with the surgical instrument 22. The surgical instrument virtual boundary is tracked via the instrument tracker 48. The surgical instrument virtual boundary may be defined merely by a model of the surgical instrument 22. The manipulator controller 54 then monitors movement of the surgical instrument virtual boundary relative to the other virtual constraint boundaries, including the virtual cutting boundaries and other virtual constraint boundaries associated with other objects. The manipulator controller 54 is then programmed to continuously track movement of the boundaries and update guidance of the surgical instrument 22 as the boundaries move relative to the surgical instrument 22.

Objects to be avoided by the surgical instrument 22 in the operating room may be tracked indirectly by associating the object with one or more trackers that are not directly fixed to the object. For instance, in FIG. 4, the opening 106 in the tissue, although not directly attached to a tracker, is formed by the retractor assemblies 104 with trackers 110 fixed thereto. Since the retractor assemblies 104 form the opening 106, there is a general correlation between the size and shape of the opening 106 and the position and orientation of the retractor assemblies 104, which can be tracked by the navigation system 20 using the trackers 110, as described above. Therefore, the opening 106 can also be dynamically tracked.

The opening 106 can be defined in the boundary creation software module using the points associated with the retractor assemblies 104 since the opening 106 lies along an edge of the retractor assemblies 104. Alternatively, the opening 106 can be traced using the pointer P. In the latter case, the pointer P is used to capture points defining a periphery of the opening 106 such that the points can be connected in the boundary creation software module to form a ring representing the opening 106. The ring may be defined in the boundary creation software module as a virtual constraint boundary to constrain movement of the surgical instrument 22 to within the ring in accordance with the robotic control functionality associated with such openings described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The opening 106 could additionally be registered to the trackers 110 so that movement of the opening 106 is trackable using the trackers 110. Other tissues to be avoided by the surgical instrument 22 such as nerve tissue, ligaments, and the like can similarly be outlined by the pointer P and associated with the trackers 110 to track their movement.

Figure 5:
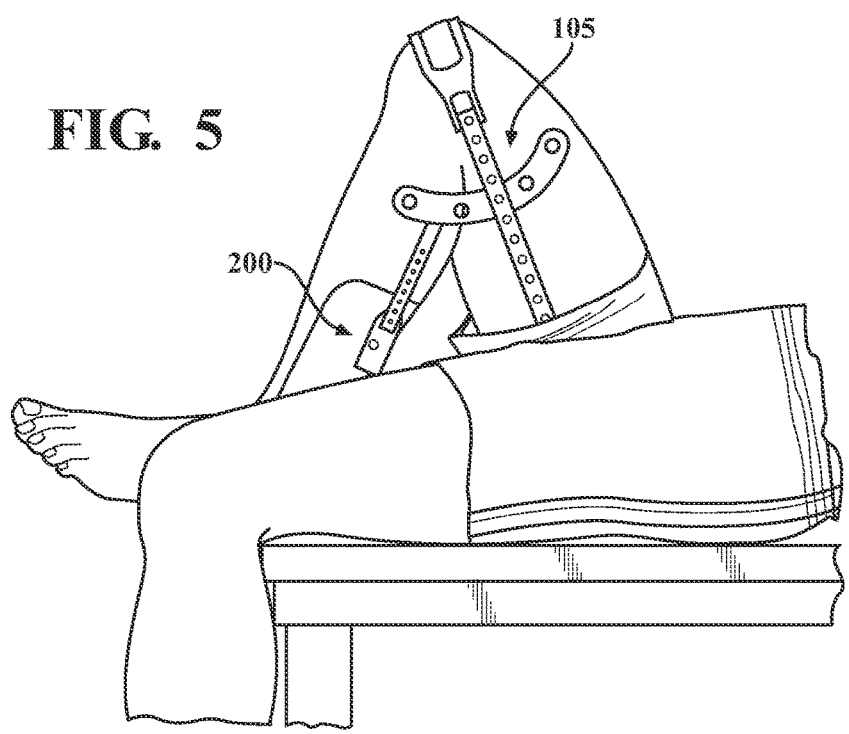
FIG. 5 is an elevational view of a leg holder and retractor assembly being used to maintain the tissue opening.

Referring to FIG. 5, a leg holder 200 for supporting a leg of a patient is shown. The leg holder 200 is described in more detail in U.S. patent application Ser. No. 13/554,010, entitled, "Multi-position Limb Holder", published as U.S. Patent Application Publication No. 2013/0019883, hereby incorporated by reference. An alternative retractor assembly 105 for attaching to the leg holder 200 is shown in FIG. 5.

The alternative retractor assembly 105 is described in more detail in U.S. patent application Ser. No. 13/554,010, hereby incorporated by reference.

Figure 6:
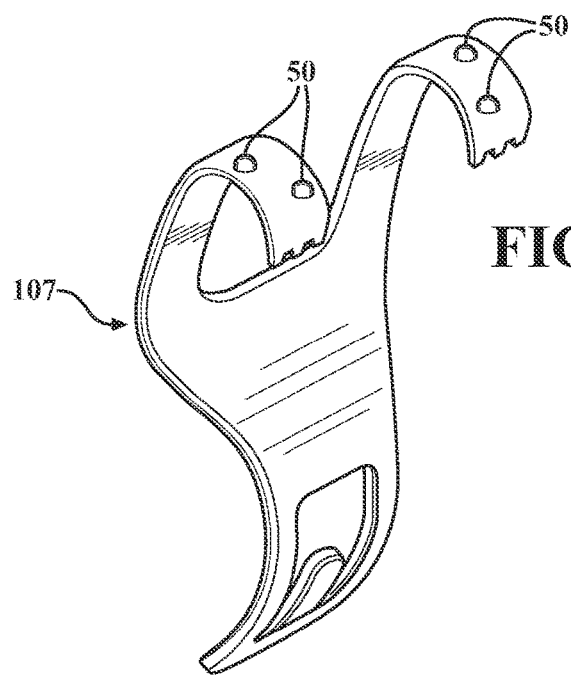
FIG. 6 is a top perspective view of a retractor.
Figure 7:
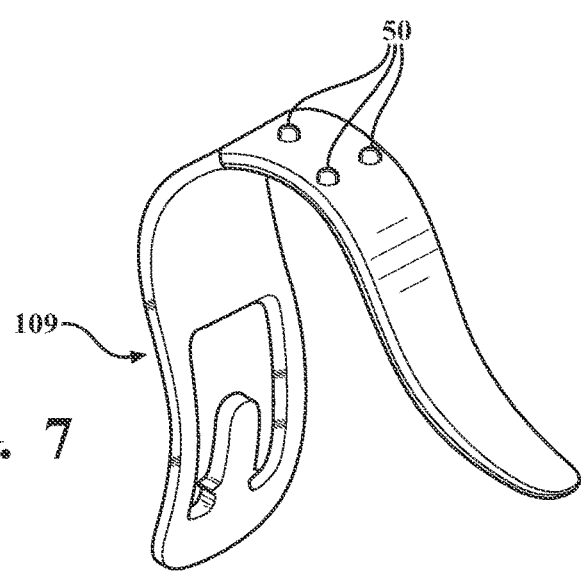
FIG. 7 is a top perspective view of an alternative retractor.

Retractor heads 107, 109 in FIGS. 6 and 7 can be used to retract soft tissue to access bone in a surgical procedure. Use of these types of heads 107, 109 for retracting tissue is described in more detail in U.S. patent application Ser. No. 13/554,010, hereby incorporated by reference. In FIGS. 6 and 7, tracking elements are fixed to the heads 107, 109 so that the heads 107, 109 can be tracked by the navigation system 20. In the embodiment shown, the tracking elements are three or more LEDs 50 that are integrated into the structure of each of the heads 107, 109 and fixed in relationship to one another. The geometric model of each head 107, 109 in relation to the LEDs 50 is also stored on the retractor head 107, 109 in memory (not shown) and can be transmitted to the camera unit 36 via transceivers (including transceiver, not shown, integrated into the retractor head 107, 109). Alternatively, the model of each head is pre-stored in the navigation computer 26 and accessed during navigation setup by identifying a type or serial no. of the retractor head 107, 109 using the boundary creation software module. The shape of each retractor head 107, 109 can also be identified by correlating a unique LED pattern on the retractor head 107, 109 to a database of retractor head shapes.

By creating virtual constraint boundaries associated with the shapes of the retractor assemblies 104 and tracking movement of the virtual constraint boundaries using trackers 110 or integrated tracking elements, the manipulator controller 54 can guide movement of the surgical instrument 22 with respect to the retractor virtual constraint boundaries and the virtual cutting boundaries so that the surgical instrument 22 is not moved beyond these boundaries thereby avoiding inadvertent contact with the retractor assemblies 104 or with bone or other tissue to remain after the surgery. These virtual boundaries may be used in both a manual mode and semi-autonomous mode of the surgical manipulator as described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference.

Figure 8:
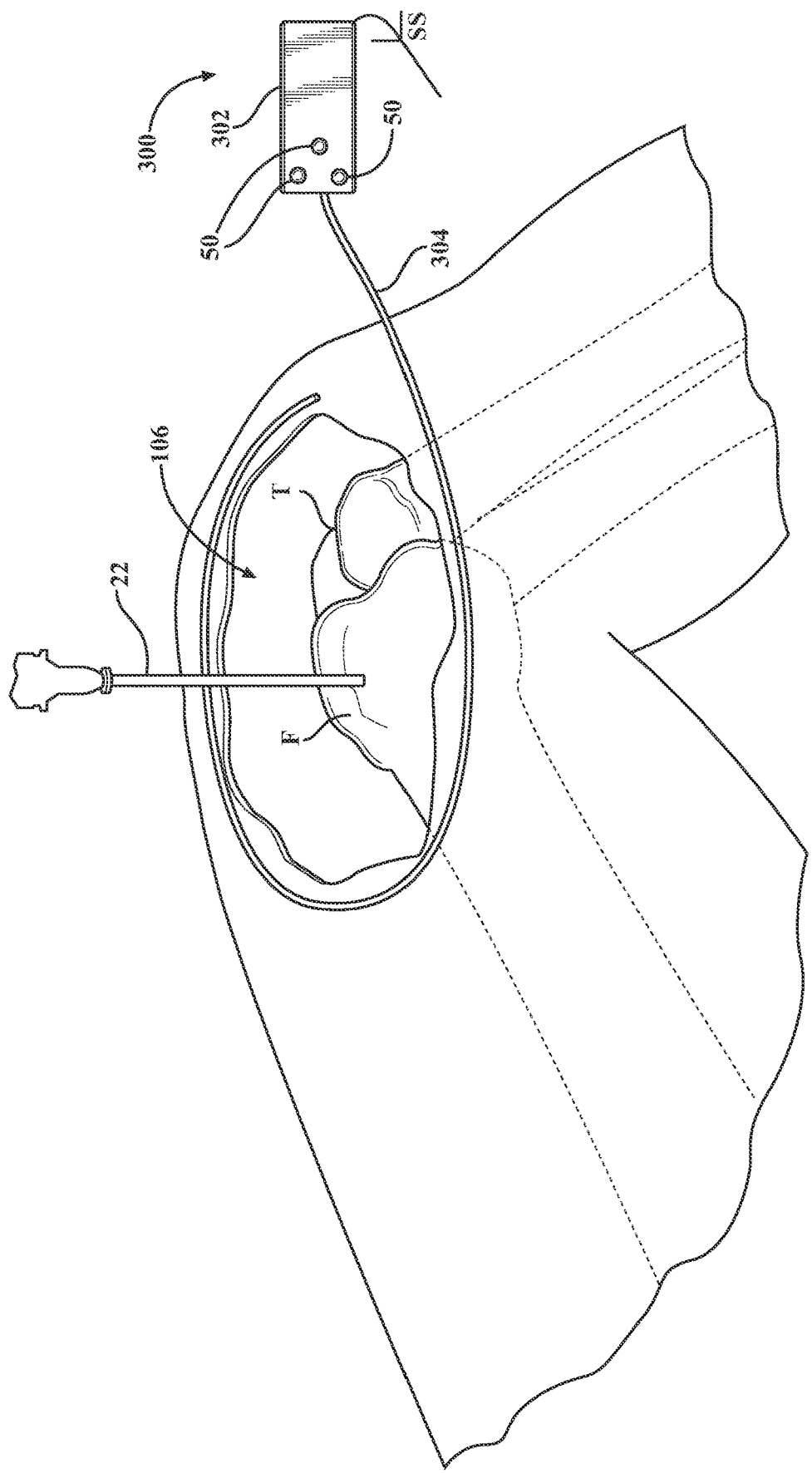
FIG. 8 is a top perspective view of the tissue opening showing an end effector in the tissue opening and a flexible shape sensing device for tracking movement of the tissue opening.

Referring to FIG. 8, a flexible shape sensing device 300 may also be used to determine a position of an object, such as opening 106. The flexible shape sensing device 300 includes a housing 302 having its own shape sensing coordinate system SS. The housing 302 forms part of a reflectometer, such as the Distributed Sensing System commercially available from Luna Innovations Incorporated of Roanoke, Virginia. Another example of a commercially available reflectometer is the Optical Backscatter Reflectometer from Luna Innovations Incorporated.

A fiber optic cable 304 extends from the housing 302 and is laid on the patient's skin about the opening 106 in close proximity to the opening 106. In some embodiments, the cable 304 is adhered to the skin in a perimeter with an offset from the opening 106. In some embodiments, the offset is less than five millimeters from the opening 106 at all locations along the perimeter of the opening 106. In other embodiments, different offsets may be used or the offsets may be measured after placing the fiber optic cable 304 so that the location of the fiber optic cable 304 relative to the opening 106 is known. The cable 304 is flexible so that as the shape of the opening 106 changes, the shape of the cable 304 also changes. Position of the cable 304 is able to be dynamically tracked. The flexible shape sensing device 300 including the reflectometer, cable, and other features, and their method of use for determining position are described in U.S. Pat. No. 7,772,541 to Froggatt et al., hereby incorporated by reference.

Tracking elements, such as LEDs 50 may be integrated into the flexible shape sensing device 300. Alternatively, a tracker (not shown) can be mounted to the housing 302. The LEDs 50 integrated into the flexible shape sensing device 300 transmit signals to the camera unit 36 in the same manner as the LEDs 50 of the trackers 44, 46, 48. Accordingly, the position and orientation of the housing 302 and the shape sensing coordinate system SS can be determining by the navigation system 20 in the localizer coordinate system LCLZ. Movement of the cable 304 results in changes in position in shape sensing coordinate system SS, which is fixed with respect to housing 302. Coordinate system SS is registered to the localizer coordinate system LCLZ using the LEDs 50 on the housing 302. Once registered, changes in position of the cable 304 can also be determined in the localizer coordinate system LCLZ.

The opening 106 may be defined in the boundary creation software module as a virtual constraint boundary to constrain movement of the surgical instrument 22 to within the opening 106 in accordance with the robotic control functionality associated with such openings described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. Other tissues to be avoided by the surgical instrument 22 such as nerve tissue, ligaments, and the like can similarly be tracked using flexible shape sensing devices 300. Likewise, flexible shape sensing devices 300 could be used to establish other boundaries, such as being integrated into gloves worn by the surgical staff so that boundaries associated with surgical personnel can be created.

Figure 9:
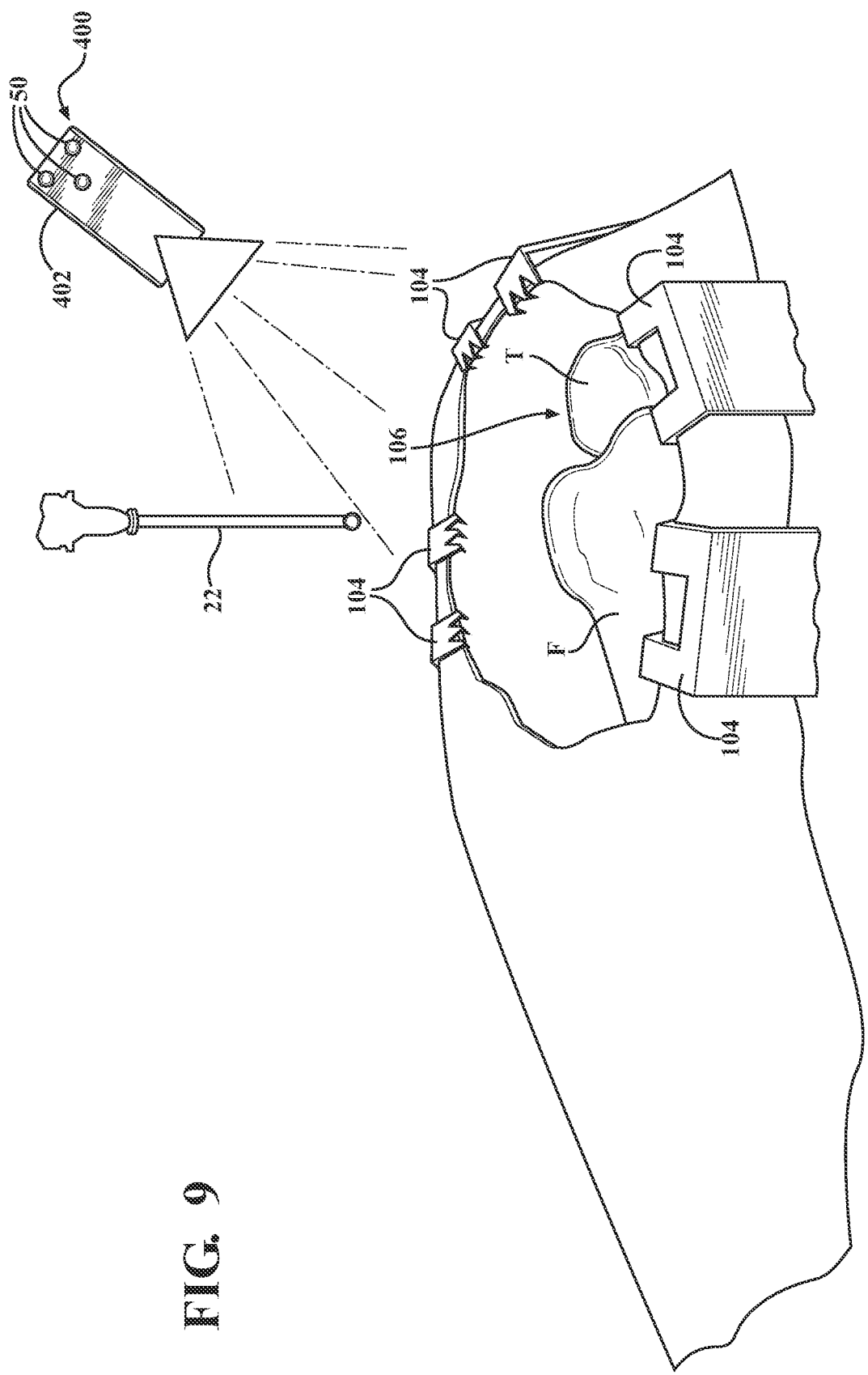
FIG. 9 is a top perspective view of the tissue opening showing an end effector in the tissue opening and a machine vision system for tracking movement of the tissue opening.

Machine vision can identify objects in the operating room and create virtual constraint boundaries associated with the objects. FIG. 9 shows a machine vision system 400. Machine vision system 400 includes a 3-dimensional machine vision camera 402. The vision camera 402 is arranged so that a field-of-view of the vision camera 402 encompasses the surgical site and objects in proximity to the surgical site. As shown in FIG. 9, such objects may include the surgical instrument 22 (shown as a cutting bur), retractor assemblies 104, femur F, and tibia T. The machine vision system 400 has a control unit (not shown) in communication with the vision camera 402. The control unit includes a processor, memory, and storage and is in communication with the navigation computer 26.

Initially, the objects to be tracked are identified. The objects may be identified by selecting objects stored in memory on the control unit using machine vision software. For instance, groups of pixels associated with different sizes and shapes of retractor assemblies 104 may be stored in the control unit. By selecting one of the retractor assemblies 104 to be tracked the machine vision software identifies the corresponding group of pixels and the machine vision software then operates to detect like groups of pixels using conventional pattern recognition technology.

Alternatively, the objects can be identified using an interface in which a user outlines or selects the objects to be tracked on the displays 28, 29. For instance, images taken by the vision camera 402 from overhead the surgical site—similar to the image shown in FIG. 9—are displayed on the displays 28, 29. The user then, using a mouse, digital pen, or the like, traces objects to be tracked on the display 28, 29. The machine vision software stores the pixels associated with the object that was traced into its memory. The user identifies each object by a unique identifier such as naming the object "MEDIAL RETRACTOR", etc. in the machine vision software so that the saved group of pixels is now associated with the unique identifier. Multiple objects could be stored in this manner. The machine vision system 400 utilizes conventional pattern recognition and associated software to later detect these objects.

The machine vision system 400 is able to detect movement of these objects by continuously taking images, reviewing the images, and detecting movement of the groups of pixels associated with the objects. In some cases, position information from the control unit of the machine vision system 400 for the objects can be transmitted to the navigation computer 26. Likewise, position information from the navigation computer 26 can be transmitted from the navigation computer 26 to the control unit of the machine vision system 400.

Control unit of the machine vision system 400 may provide position information for the objects in a machine vision coordinate system MV. The vision camera 402 also includes LEDs 50 so that the camera unit 36 can track and thus register the position and orientation of the machine vision coordinate system MV relative to the localizer coordinate system LCLZ. Thus, position information from the vision camera 402 can be determined in the localizer coordinate system LCLZ. Virtual boundaries can thus be associated with the objects in the machine vision system 400 and information relating to these virtual boundaries can be communicated to the navigation computer 26. Additionally, information relating to the virtual constraint boundaries can be forwarded to the manipulator controller 54 to guide the manipulator 56 and corresponding movement of the surgical instrument 22 relative to these virtual boundaries.

The objects can also be initially registered to the localizer coordinate system LCLZ using the pointer P. For instance, when the retractor assemblies 104 are not equipped with trackers 110 or integrated tracking elements, the pointer P may be used to initially establish virtual constraint boundaries associated with the retractor assemblies 104 when the retractor assemblies 104 are at rest, i.e., not moving. These virtual constraint boundaries would then be stored in the navigation computer 26 and/or manipulator controller 54 for use in guiding the robotic manipulator 56. The machine vision system 400 would also be configured to detect movement of the retractor assemblies 104 as previously described, i.e., by tracking movement of the groups of pixels associated with the retractor assemblies 104.

Machine vision detection of movement of a retractor assembly 104 could then be used to shift the virtual constraint boundary stored in the navigation computer for the retractor assembly 104 by defining a change in pose of the retractor assembly 104 (e.g., translation along 3 axes/rotation about 3 axes). The machine vision system 400 would operate to establish a first pose of the retractor assembly 140 at time t1 and a second pose at time t2. The difference in pose between t1 and t2 would be provided to the navigation computer 26 and/or manipulator controller 54 to move the associated virtual constraint boundary by a proportional amount in the localizer coordinate system LCLZ. In some embodiments, only 2-dimensional movement is detected by the vision camera 402 and shared with the navigation computer 26 and/or manipulator controller 54 to update a position of the retractor assembly 104.

In some embodiments, the robotic system is a robotic surgical cutting system for cutting away material from a patient's anatomy, such as bone or soft tissue. Once the cutting system is determined to be in the proper position by the navigation system 20, the cutting system cuts away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation", the disclosure of which is hereby incorporated by reference. The navigation system 20 instructs the surgeon on proper procedures for locating these implants on bone and securing the implants in position, including the use of trial implants.

In other systems, the instrument 22 has a cutting tool that is movable in three degrees of freedom relative to a handheld housing and is manually positioned by the hand of the surgeon, without the aid of cutting jigs, guide arms or other constraining mechanism. Such systems are shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference.

In these embodiments, the system includes a hand held surgical cutting instrument having a cutting tool. A control system controls movement of the cutting tool in at least three degrees of freedom using internal actuators/motors, as shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference. The navigation system 20 communicates with the control system. One tracker (such as tracker 48) is mounted to the instrument. Other trackers (such as trackers 44, 46) are mounted to a patient's anatomy. The navigation system 20 communicates with the control system of the hand held surgical cutting instrument. The navigation system 20 communicates position and/or orientation data to the control system. The position and/or orientation data is indicative of a position and/or orientation of the instrument 22 relative to the anatomy. This communication provides closed loop control to control cutting of the anatomy such that the cutting occurs within a predefined boundary (the term predefined boundary is understood to include predefined trajectory, volume, line, other shapes or geometric forms, and the like).

In some embodiments, a 3-D video camera (not shown) is attached to the camera unit 36. The video camera is oriented such that a field of view of the camera unit 36 can be associated with the field of view of the video camera. In other words, the two fields of view may be matched or otherwise correlated such that if an object can be seen in video images streamed from the video camera, the objects are also within the field of view of the camera unit 36. A coordinate system of the video camera can also be transformed into the localizer coordinate system LCLZ or vice versa so that positions and/or orientations of objects shown in the video images streamed from the video camera are known in the localizer coordinate system LCLZ. Video images from the video camera can be streamed to the displays 28, 29 and the user can then identify on the displays 28, 29, using an input device, such as a mouse or touch screen, virtual constraint boundaries to delineate zones to be avoided by the instrument 22. The video images could be provided in 2-D or in 3-D to facilitate the creation of these virtual constraint boundaries. Information relating to the positions and/or orientation of these virtual constraint boundaries would be provided into the localizer coordinate system LCLZ and tracked by the navigation computer 26 or manipulator controller 54, for example, to prevent the instrument 22 from intruding on the boundaries created.

In some embodiments, when the manipulator controller 54 or navigation computer 26 detect that the instrument 22 is approaching one of the virtual constraint boundaries, an alarm may be generated. The alarm may include visual, tactile, or audible feedback to the user that indicates to the user that the object associated with the virtual constraint boundary is about to be struck and/or may include visual, tactile, or audible indications of distance from the object or associated virtual constraint boundaries.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system comprising:
    a robotic manipulator;
    a surgical instrument coupled to the robotic manipulator and being moveable by the robotic manipulator;
    a navigation system comprising:
        a first tracker coupled to a first bone;
        a second tracker coupled to a second bone, wherein the first bone and the second bone are moveable relative to each other; and
        a localizer configured to track each of the first tracker, the second tracker, and the surgical instrument; and
    one or more controllers configured to:
        associate a first virtual boundary with the first bone;
        associate a second virtual boundary with the second bone; and
        control the robotic manipulator in relation to the first virtual boundary to facilitate manipulation of the first bone by the surgical instrument and simultaneously control the robotic manipulator in relation to the second virtual boundary to avoid interaction of the surgical instrument with the second bone while accounting for movement of the first virtual boundary and the second virtual boundary relative to each other that is based on the tracked first and second trackers.

2. The surgical system of claim 1, wherein the one or more controllers:
    control the robotic manipulator in relation to the first virtual boundary by being configured to constrain movement of the surgical instrument relative to the first virtual boundary; and
    control the robotic manipulator in relation to the second virtual boundary by being configured to constrain movement of the surgical instrument relative to the second virtual boundary.

3. The surgical system of claim 1, wherein:
    the first virtual boundary delineates a first portion of the first bone for which manipulation by the surgical instrument is allowed from a second region of the first bone for which interaction by the surgical instrument is protected; and
    the one or more controllers control the robotic manipulator in relation to the first virtual boundary to facilitate manipulation of the first bone by the surgical instrument to remove the first portion of the first bone.

4. The surgical system of claim 1, wherein:
    the first bone is a femur bone; and
    the second bone is a tibia bone.

5. The surgical system of claim 1, further comprising a display and wherein, based on tracking data from the navigation system, the one or more controllers are configured to provide, on the display, image representations of the surgical instrument, the first bone, the first virtual boundary, the second bone, and the second virtual boundary.

6. The surgical system of claim 1, wherein the one or more controllers are configured to selectively control operation of the robotic manipulator in a manual mode and a semi-autonomous mode.

7. The surgical system of claim 1, wherein the one or more controllers are configured to produce tactile feedback in response to constrained movement of the surgical instrument relative to one or both of the first virtual boundary and second virtual boundary.

8. The surgical system of claim 1, wherein the surgical instrument is further defined as a cutting tool.

9. A method of operating a surgical system, the surgical system comprising one or more controllers, a robotic manipulator, a surgical instrument coupled to the robotic manipulator and being moveable by the robotic manipulator, and a navigation system including a first tracker coupled to a first bone, a second tracker coupled to a second bone, and a localizer configured to track each of the first tracker, the second tracker, and the surgical instrument, wherein the first bone and the second bone are moveable relative to each other, the method comprising the one or more controllers:
    associating a first virtual boundary with the first bone;
    associating a second virtual boundary with the second bone; and
    controlling the robotic manipulator in relation to the first virtual boundary to facilitate manipulation of the first bone by the surgical instrument and simultaneously controlling the robotic manipulator in relation to the second virtual boundary to avoid interaction of the surgical instrument with the second bone while accounting for movement of the first virtual boundary and the second virtual boundary relative to each other that is based on the tracked first and second trackers.

10. The method of claim 9, comprising the one or more controllers:
    controlling the robotic manipulator in relation to the first virtual boundary by constraining movement of the surgical instrument relative to the first virtual boundary; and
    controlling the robotic manipulator in relation to the second virtual boundary by constraining movement of the surgical instrument relative to the second virtual boundary.

11. The method of claim 9, wherein the first virtual boundary delineates a first portion of the first bone for which manipulation by the surgical instrument is allowed from a second region of the first bone for which interaction by the surgical instrument is protected; and comprising the one or more controllers:
    controlling the robotic manipulator in relation to the first virtual boundary to facilitate manipulation of the first bone by the surgical instrument to remove the first portion of the first bone.

12. The method of claim 9, wherein the surgical system further comprises a display; and comprising the one or more controllers:

providing, on the display, and based on tracking data from the navigation system, image representations of the surgical instrument, the first bone, the first virtual boundary, the second bone, and the second virtual boundary.

13. The method of claim 9, comprising the one or more controllers producing tactile feedback in response to constraining movement of the surgical instrument relative to one or both of the first virtual boundary and second virtual boundary.

14. A non-transitory computer readable medium configured for a surgical system, the surgical system comprising one or more controllers, a robotic manipulator, a surgical instrument coupled to the robotic manipulator and being moveable by the robotic manipulator, and a navigation system including a first tracker coupled to a first bone, a second tracker coupled to a second bone, and a localizer configured to track each of the first tracker, the second tracker, and the surgical instrument, wherein the first bone and the second bone are moveable relative to each other, the non-transitory computer readable medium comprising instructions, which when executed by the one or more controllers, are configured to:

associate a first virtual boundary with the first bone;

associate a second virtual boundary with the second bone; and control the robotic manipulator in relation to the first virtual boundary to facilitate manipulation of the first bone by the surgical instrument and simultaneously control the robotic manipulator in relation to the second virtual boundary to avoid interaction of the surgical instrument with the second bone while accounting for movement of the first virtual boundary and the second virtual boundary relative to each other that is based on the tracked first and second trackers.

* * * * *